(12) United States Patent
Arumugasamy et al.

(10) Patent No.: US 11,299,469 B2
(45) Date of Patent: Apr. 12, 2022

(54) NAPHTHOFURAN DERIVATIVES, PREPARATION, AND METHODS OF USE THEREOF

(71) Applicant: Sumitomo Dainippon Pharma Oncology, Inc., Cambridge, MA (US)

(72) Inventors: Jeevanandam Arumugasamy, Boxborough, MA (US); Wei Li, Wayland, MA (US)

(73) Assignee: Sumitomo Dainippon Pharma Oncology, Inc., Cambridge, MA (US)

( * ) Notice: Subject to any disclaimer, the term of this patent is extended or adjusted under 35 U.S.C. 154(b) by 9 days.

(21) Appl. No.: 16/464,413

(22) PCT Filed: Nov. 29, 2017

(86) PCT No.: PCT/US2017/063734
§ 371 (c)(1),
(2) Date: May 28, 2019

(87) PCT Pub. No.: WO2018/102427
PCT Pub. Date: Jun. 7, 2018

(65) Prior Publication Data
US 2021/0107883 A1    Apr. 15, 2021

Related U.S. Application Data

(60) Provisional application No. 62/427,441, filed on Nov. 29, 2016.

(51) Int. Cl.
C07D 307/92    (2006.01)
C07C 249/02    (2006.01)

(52) U.S. Cl.
CPC .......... *C07D 307/92* (2013.01); *C07C 249/02* (2013.01)

(58) Field of Classification Search
None
See application file for complete search history.

(56) References Cited

U.S. PATENT DOCUMENTS

| | | | |
|---|---|---|---|
| 2,472,133 A | 6/1949 | Viktor et al. | |
| 4,778,805 A | 10/1988 | Adams et al. | |
| 5,166,315 A | 11/1992 | Summerton et al. | |
| 5,595,721 A | 1/1997 | Kaminski et al. | |
| 5,677,095 A | 10/1997 | Kikuchi et al. | |
| 5,736,137 A | 4/1998 | Anderson et al. | |
| 5,846,534 A | 12/1998 | Waldmann et al. | |
| 6,235,883 B1 | 5/2001 | Jakobovits et al. | |
| 6,337,346 B1 | 1/2002 | Lee et al. | |
| 6,395,773 B1 | 5/2002 | Hirai et al. | |
| 6,682,736 B1 | 1/2004 | Hanson et al. | |
| 6,734,203 B2 | 5/2004 | Matsuhisa et al. | |
| 6,828,337 B2 | 12/2004 | Belloni et al. | |
| 6,984,720 B1 | 1/2006 | Korman et al. | |
| 6,994,862 B2 | 2/2006 | Jeong et al. | |
| 7,019,147 B1 | 3/2006 | Barth et al. | |
| 7,090,843 B1 | 8/2006 | Francisco et al. | |
| 7,169,901 B2 | 1/2007 | Baca et al. | |
| 7,422,739 B2 | 9/2008 | Anderson et al. | |
| 7,435,797 B2 | 10/2008 | Lowman et al. | |
| 7,538,234 B2 | 5/2009 | Iida et al. | |
| 7,560,111 B2 | 7/2009 | Kao et al. | |
| 7,572,442 B2 | 8/2009 | Thorpe et al. | |
| 7,691,977 B2 | 4/2010 | Fuh et al. | |
| 7,758,859 B2 | 7/2010 | Fuh et al. | |
| 7,807,798 B2 | 10/2010 | Jakobovits et al. | |
| 7,824,679 B2 | 11/2010 | Hanson et al. | |
| 7,910,104 B2 | 3/2011 | Carr et al. | |
| 7,910,752 B2 | 3/2011 | Tokuda et al. | |
| 7,943,743 B2 | 5/2011 | Korman et al. | |

(Continued)

FOREIGN PATENT DOCUMENTS

| | | |
|---|---|---|
| AU | 2015218436 | 9/2015 |
| AU | 2017203239 | 6/2017 |

(Continued)

OTHER PUBLICATIONS

Lemma et al., "Phase II Study of Carboplatin and Paclitaxel in Advanced Thymoma and Thymic Carcinoma," J. Clin. Oncol., 2011, 29(15):2060-2065.

(Continued)

*Primary Examiner* — Joseph R Kosack
(74) *Attorney, Agent, or Firm* — Fish & Richardson P.C.

(57) ABSTRACT

Provided herein are methods of preparation of I by reacting i with acid where $R_1$ and $R_2$ are each independently a leaving group. Intermediates to make i are also claimed.

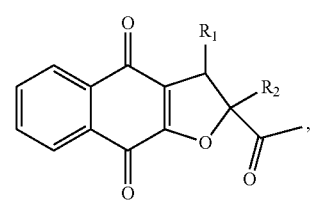

i

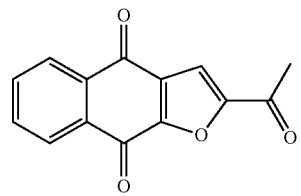

I

22 Claims, No Drawings

(56) References Cited

U.S. PATENT DOCUMENTS

| | | |
|---|---|---|
| 8,008,449 B2 | 8/2011 | Korman et al. |
| 8,101,177 B2 | 1/2012 | Fuh et al. |
| 8,119,775 B2 | 2/2012 | Moretta et al. |
| 8,143,379 B2 | 3/2012 | Hanson et al. |
| 8,168,179 B2 | 5/2012 | Honjo et al. |
| 8,217,149 B2 | 7/2012 | Irving et al. |
| 8,217,176 B2 | 7/2012 | Oguro |
| 8,354,509 B2 | 1/2013 | Carven et al. |
| 8,440,190 B2 | 5/2013 | Waldmann et al. |
| 8,529,902 B2 | 9/2013 | Teeling et al. |
| 8,617,554 B2 | 12/2013 | Roberts et al. |
| 8,623,357 B2 | 1/2014 | Waldmann et al. |
| 8,685,394 B2 | 4/2014 | Jure-Kunkel |
| 8,716,452 B2 | 5/2014 | Jure-Kunkel |
| 8,779,108 B2 | 7/2014 | Queva et al. |
| 8,784,815 B2 | 7/2014 | Korman et al. |
| 8,802,091 B2 | 8/2014 | Johnson et al. |
| 8,877,803 B2 | 11/2014 | Jiang et al. |
| 8,900,587 B2 | 12/2014 | Carven et al. |
| 8,952,136 B2 | 2/2015 | Carven et al. |
| 8,977,803 B2 | 3/2015 | Horn et al. |
| 8,981,065 B2 | 3/2015 | Moretta et al. |
| 9,062,113 B2 | 6/2015 | Weber et al. |
| 9,084,766 B2 | 7/2015 | Li et al. |
| 9,096,672 B2 | 8/2015 | Weber et al. |
| 9,102,725 B2 | 8/2015 | Korman et al. |
| 9,150,530 B2 | 10/2015 | Jiang et al. |
| 9,150,656 B2 | 10/2015 | Johnson et al. |
| 9,212,224 B2 | 12/2015 | Cogswell et al. |
| 9,220,776 B2 | 12/2015 | Sharma et al. |
| 9,328,345 B2 | 5/2016 | Li et al. |
| 9,381,184 B2 | 7/2016 | Li et al. |
| 9,730,909 B2 | 8/2017 | Li et al. |
| 9,732,055 B2 | 8/2017 | Li et al. |
| 9,745,278 B2 | 8/2017 | Li et al. |
| 9,795,595 B2 | 10/2017 | Li et al. |
| 9,834,532 B2 | 12/2017 | Jang et al. |
| 10,017,488 B2 | 7/2018 | Li et al. |
| 10,377,731 B2 | 8/2019 | Li et al. |
| 10,543,189 B2 | 1/2020 | Li et al. |
| 10,646,464 B2 | 5/2020 | Li et al. |
| 10,683,274 B2 | 6/2020 | Li et al. |
| 10,851,075 B2 | 12/2020 | Li et al. |
| 10,934,309 B2 | 3/2021 | Li et al. |
| 2004/0006009 A1 | 1/2004 | Larsen et al. |
| 2004/0092428 A1 | 5/2004 | Chen et al. |
| 2004/0138140 A1 | 7/2004 | Xu et al. |
| 2004/0138189 A1 | 7/2004 | Sebti et al. |
| 2005/0010060 A1 | 1/2005 | Blokhin et al. |
| 2005/0049207 A1 | 3/2005 | Kaufmann |
| 2006/0019256 A1 | 1/2006 | Clarke et al. |
| 2006/0099251 A1 | 5/2006 | Johannsson |
| 2006/0142271 A1 | 6/2006 | Muller et al. |
| 2006/0222696 A1 | 10/2006 | Okada et al. |
| 2006/0247318 A1 | 11/2006 | Song et al. |
| 2006/0252674 A1 | 11/2006 | Peritt et al. |
| 2006/0279011 A1 | 12/2006 | Palakodaty et al. |
| 2007/0009532 A1 | 1/2007 | Sikic et al. |
| 2007/0060521 A1 | 3/2007 | Jove et al. |
| 2007/0123502 A1 | 5/2007 | Turkson et al. |
| 2007/0207980 A1 | 9/2007 | Salama et al. |
| 2007/0238770 A1 | 10/2007 | Gougoutas et al. |
| 2009/0042977 A1 | 2/2009 | Tokuda et al. |
| 2010/0297118 A1 | 11/2010 | Macdougal et al. |
| 2010/0310503 A1 | 12/2010 | Li et al. |
| 2011/0008331 A1 | 1/2011 | Triebel |
| 2011/0112180 A1 | 5/2011 | Jiang et al. |
| 2012/0077986 A1 | 3/2012 | Iida et al. |
| 2012/0252763 A1 | 10/2012 | Li et al. |
| 2013/0028944 A1 | 1/2013 | Li et al. |
| 2013/0034591 A1 | 2/2013 | Li et al. |
| 2015/0018410 A1 | 1/2015 | Jiang et al. |
| 2015/0183756 A1 | 7/2015 | Li et al. |
| 2015/0307609 A1 | 10/2015 | Lonberg et al. |
| 2016/0030384 A1 | 2/2016 | Li et al. |
| 2016/0060344 A1 | 3/2016 | Narwal et al. |
| 2016/0220494 A1 | 8/2016 | Stroyer et al. |
| 2016/0271099 A1 | 9/2016 | Li et al. |
| 2016/0339001 A1 | 11/2016 | Li et al. |
| 2017/0015677 A1 | 1/2017 | Ban et al. |
| 2017/0174646 A1 | 6/2017 | Sone et al. |
| 2017/0197932 A1 | 7/2017 | Jiang et al. |
| 2017/0319537 A1 | 11/2017 | Li et al. |
| 2018/0030021 A1 | 2/2018 | Li et al. |
| 2018/0030022 A1 | 2/2018 | Li et al. |
| 2018/0085341 A1 | 3/2018 | Li et al. |
| 2018/0098959 A1 | 4/2018 | Li et al. |
| 2018/0140572 A1 | 5/2018 | Li et al. |
| 2018/0193303 A1 | 7/2018 | Li et al. |
| 2018/0250260 A1 | 9/2018 | Li et al. |
| 2018/0250261 A1 | 9/2018 | Li et al. |
| 2018/0333385 A1 | 11/2018 | Li et al. |
| 2019/0076392 A1 | 3/2019 | Li et al. |
| 2019/0135773 A1 | 5/2019 | Li et al. |
| 2019/0224157 A1 | 7/2019 | Li et al. |
| 2019/0231735 A1 | 8/2019 | Li et al. |
| 2019/0241535 A1 | 8/2019 | Sone et al. |
| 2019/0241583 A1 | 8/2019 | Ban et al. |
| 2019/0249134 A1 | 8/2019 | Li et al. |
| 2019/0263768 A1 | 8/2019 | Jiang et al. |
| 2019/0375723 A1 | 12/2019 | Li et al. |
| 2019/0388382 A1 | 12/2019 | Li et al. |
| 2020/0039948 A1 | 2/2020 | Li et al. |
| 2020/0237711 A1 | 7/2020 | Li et al. |
| 2020/0397740 A1 | 12/2020 | Li et al. |
| 2021/0024482 A1 | 1/2021 | Li et al. |
| 2021/0115006 A1 | 4/2021 | Li |

FOREIGN PATENT DOCUMENTS

| | | |
|---|---|---|
| CA | 2107806 | 4/1994 |
| CA | 2959931 | 9/2011 |
| CA | 2959951 | 9/2011 |
| EP | 0466094 | 1/1992 |
| EP | 0592366 | 4/1994 |
| EP | 1897540 | 3/2008 |
| EP | 2436669 | 4/2012 |
| EP | 3108750 | 12/2016 |
| EP | 3127907 | 2/2017 |
| JP | 63196576 | 8/1988 |
| JP | 04139177 | 5/1992 |
| JP | H 09249560 | 9/1997 |
| JP | 1121284 | 1/1999 |
| JP | 1165141 | 3/1999 |
| JP | 2004224802 | 8/2004 |
| JP | 2007-502301 | 2/2007 |
| JP | 2007145680 | 6/2007 |
| JP | 2010-538091 | 12/2010 |
| JP | 2012092083 | 5/2012 |
| JP | 2014-098034 | 5/2014 |
| JP | 2016016973 | 2/2016 |
| JP | 6199787 | 9/2017 |
| JP | 2019-011369 | 1/2019 |
| JP | 2019110987 | 6/2019 |
| SU | 1049490 | 10/1983 |
| WO | WO 99/62909 | 12/1999 |
| WO | WO 00/44774 | 8/2000 |
| WO | WO 2000/059473 | 10/2000 |
| WO | WO 01/23372 | 4/2001 |
| WO | WO 2001/060803 | 8/2001 |
| WO | WO 01/168139 | 9/2001 |
| WO | WO 2004/024145 | 3/2004 |
| WO | WO 2004/026253 | 4/2004 |
| WO | WO 2004/046120 | 6/2004 |
| WO | WO 2004/045593 | 8/2004 |
| WO | WO 2005/033048 | 4/2005 |
| WO | WO 2005/056055 | 6/2005 |
| WO | WO 2005/058829 | 6/2005 |
| WO | WO 2005/110477 | 11/2005 |
| WO | WO 2006/014359 | 2/2006 |
| WO | WO 2006/018627 | 2/2006 |
| WO | WO 2006/052712 | 5/2006 |
| WO | WO 2006/056399 | 6/2006 |
| WO | WO 2006/065894 | 6/2006 |

(56) References Cited

FOREIGN PATENT DOCUMENTS

| | | |
|---|---|---|
| WO | WO 2006/091837 | 8/2006 |
| WO | WO 2006/098355 | 9/2006 |
| WO | WO 2006/113790 | 10/2006 |
| WO | WO 2006/126505 | 11/2006 |
| WO | WO 2007/042912 | 4/2007 |
| WO | WO 2007/056470 | 5/2007 |
| WO | WO 2007/061880 | 5/2007 |
| WO | WO 2007/074347 | 7/2007 |
| WO | WO 2007/087129 | 8/2007 |
| WO | WO 2007/092620 | 8/2007 |
| WO | WO 2007/095753 | 8/2007 |
| WO | WO 2007/100640 | 9/2007 |
| WO | WO 2007/115269 | 10/2007 |
| WO | WO 2008/077062 | 6/2008 |
| WO | WO 2008/094321 | 8/2008 |
| WO | WO 2009/036059 | 3/2009 |
| WO | WO 2009/036099 | 3/2009 |
| WO | WO 2009/036101 | 3/2009 |
| WO | WO 2009/060282 | 5/2009 |
| WO | WO 2009/107850 | 9/2009 |
| WO | WO 2010/027827 | 3/2010 |
| WO | WO 2011/008331 | 1/2011 |
| WO | WO 2011/066342 | 6/2011 |
| WO | WO 2011/084694 | 7/2011 |
| WO | WO 2011/116398 | 9/2011 |
| WO | WO 2011/116399 | 9/2011 |
| WO | WO 2012/024818 | 3/2012 |
| WO | WO 2012/119265 | 9/2012 |
| WO | WO 2013/155114 | 10/2013 |
| WO | WO 2013/166618 | 11/2013 |
| WO | WO 2013/172918 | 11/2013 |
| WO | WO 2013/173223 | 11/2013 |
| WO | WO 2014/169078 | 10/2014 |
| WO | WO 2015/120304 | 8/2015 |
| WO | WO 2015/151490 | 10/2015 |
| WO | WO 2015/155673 | 10/2015 |
| WO | WO 2015/190489 | 12/2015 |
| WO | WO 2016/044234 | 3/2016 |
| WO | WO 2016/157052 | 10/2016 |
| WO | WO 2016/168856 | 10/2016 |
| WO | WO 2016/168857 | 10/2016 |
| WO | WO 2016/196935 | 12/2016 |
| WO | WO 2017/132049 | 8/2017 |
| WO | WO 2017/013865 | 5/2018 |
| WO | WO 2018/096401 | 5/2018 |
| WO | WO 2018/183089 | 10/2018 |
| WO | WO 2018/213424 | 11/2018 |
| WO | WO 2017/164379 | 1/2019 |

OTHER PUBLICATIONS

PubChem CID: 10331844, "Napabucasin," 2006, retrieved from URL <https://pubchem.ncbi.nlm.nih.gov/compound/Napabucasin>, 23 pages.
Tseng, "Thymic carcinoma: A rare cancer requiring special attention," Formosan Journal of Surgery, 2011, 44(4):136-140.
Yoh et al., "Weekly Chemotherapy with Cisplatin, Vincristine, Doxorubicin, and Etoposide Is an Effective Treatment for Advanced Thymic Carcinoma," Cancer, 2003, 98(5):926-931.
U.S. Appl. No. 16/148,561, filed Oct. 1, 2018, Li et al.
U.S. Appl. No. 16/170,756, filed Oct. 25, 2018, Li et al.
U.S. Appl. No. 16/188,924, filed Nov. 13, 2018, Li et al.
U.S. Appl. No. 16/220,636, filed Dec. 14, 2018, Li et al.
U.S. Appl. No. 16/236,948, filed Dec. 31, 2018, Li et al.
U.S. Appl. No. 16/287,775, filed Feb. 27, 2019, Li et al.
U.S. Appl. No. 16/313,748, filed Dec. 27, 2018, Li et al.
U.S. Appl. No. 16/408,187, filed May 9, 2019, Li et al.
U.S. Appl. No. 16/445,416, filed Jun. 19, 2019, Li et al.
U.S. Appl. No. 16/463,162, filed May 22, 2019, Li et al.
U.S. Appl. No. 16/577,868, filed Sep. 20, 2019, Li et al.
U.S. Appl. No. 16/586,049, filed Sep. 27, 2019, Li et al.
U.S. Appl. No. 16/590,495, filed Oct. 2, 2019, Li et al.
U.S. Appl. No. 16/591,960, filed Oct. 3, 2019, Li et al.
Achcar et al., "Expression of Activated and Latent Signal Transducer and Activator of Transcription 3 in 303 Non-Small Cell Lung Carcinomas and 44 Malignant Mesotheliomas: Possible Role for Chemotherapeutic Intervention," Arch Pathol Lab Med., 2007, 131(9):1350-60.
Ailles and Weissman, "Cancer Stem Cells in Solid Tumors," Curr Opin Biotechnol, 2007, 18(5):460-466.
Ajani et al., "Cancer Stem Cells: The Promise and the Potential," Semin Oncol., Apr. 2015, 42(1):S3-17.
Alas, S, "Inhibition of Constitutive STAT3 Activity Sensitizes Resistant Non-Hodgkin's Lymphoma and Multiple Myeloma to Chemotherapeutic Drug-Mediated Apoptosis", Clin Cancer Res, 2003, 9(1):316-26.
Al-Hajj, M., et al., "Prospective Identification of Tumorigenic Breast Cancer Cells", Proc. Natl. Acad. Sci. USA, Apr. 1, 2003, 100(7):3983-3988.
Al-Hajj and Clarke, "Self-renewal and solid tumor stem cells," Oncogene, 2004, 23(43):7274-82.
Alvarez et al., "Genome-wide analysis of STAT target genes: elucidating the mechanism of STAT-mediated oncogenesis," Cancer Biology & Therapy, 2004,3(11):1045-1050.
Alvarez et al., "Identification of a genetic signature of activated signal transducer and activator of transcription 3 in human tumors," Cancer Res., 2005, 65(12):5054-62.
Alvi, "Functional and Molecular Characterization of Mammary Side Population Cells," Breast Cancer Res, 2003, 5(1):R1-R8.
Amin, "Selective inhibition of STAT3 induces apoptosis and G(1) cell cycle arrest in ALK-positive anaplastic large cell lymphoma", Oncogene, 2004, 23(32):5426-5434.
Anderson, "The Process of Structure-Based Drug Design," Chem and Biol, 2003 10:787-797.
Anonymous, "POR cytochrome p450 oxidoreductase [Homo sapiens(human)]-Gene—NCBIOfficial Symbol Official Full Name," Jul. 1, 2019, retrieved on Aug. 21, 2019, retrieved from URL <URL:https://www.ncbi.nlm.nih.gov/gene?Db-gene&Cmd=DetailsSearch&Term=5447>, pp. 1-17.
Aoki et al., "Inhibition of STAT3 signaling induces apoptosis and decreases survivin expression in primary effusion lymphoma," Blood, 2003, 101(4):1535-1542.
Arany, "Correlation Between Pretreatment Levels of Interferon Response Genes and Clinical Responses to an Immune Response Modifier (Imiquimod) in Genital Warts," Antimicrob Agents Chemother, 2000, 44(7):1869-73.
Bandhavkar, "Cancer stem cells: a metastasizing menace!," Cancer Medicine, 2016, 5(4):649-655.
Bannwitz et al., "Synthesis and structure-activity relationships of lapacho analogues. 2. Modification of the basic naphtho[2,3-b]furan-4,9-dione, redox activation, and suppression of human keratinocyte hyperproliferation by 8-hydroxynaphtho[2,3-b]thiophene-4,9-diones," J Med Chem., Jul. 24, 2014, 57(14):6226-6239.
Barton et al., "Signal transducer and activator of transcription 3 (STAT3) activation in prostate cancer: Direct STAT3 inhibition induces apoptosis in prostate cancer lines," Mol CancerTher., 2004, 3(1):11-20.
Baumann, "Exploring the Role of Cancer Stem Cells in Radioresistance", Nat. Rev. Cancer. 8.7, (2008), 8(7):545-554.
Becourn et al., "FOLFIRI and Bevacizumab in first-line treatment for colorectal cancer patients: safety, efficacy and genetic polymorphisms," BMC Reasearch Notes, 2014, 7:260.
Benekli et al., "Constitutive activity of signal transducer and activator of transcription 3 protein in acute myeloid leukemia blasts is associated with short disease-free survival," Blood, 2002, 99(1):252-257.
Benkhart, "Role of Stat3 in Lipopolysaccharide-Induced IL-1O gene expression," J Immunol, 2000, 165(3):1612-1617.
Berge et al., "Pharmaceutical Salts," J Pharma Sci, 1977, 66:1-19.
Berishaj et al., "Stat3 is tyrosine-phosphorylated through the interleukin-6/glycoprotein 130/Janus kinase pathway in breast cancer," Breast Cancer Res., 2007, 9(3):R32.
Blaskovich et al., "Discovery of JSI-124 (cucurbitacin I), a selective Janus kinase/signal transducer and activator of transcription 3

(56) References Cited

OTHER PUBLICATIONS signaling pathway inhibitor with potent antitumor activity against human and murine cancer cells in mice," Cancer Res, 2003, 63(6):1270-1279.
Bleau, "New Strategy for the analysis of phenotypic marker antigens in brain tumor-derived neurospheres in mice and humans", Neurosurg Focus, 2008,24(3-4):E28.
Boman et al., "Human colon cancer stem cells: a new paradigm in gastrointestinal oncology," J Clin Oncol., 2008, 26(17): 2828-2838.
Boman et al., "Cancer stem cells: a step toward the cure," J Clin Oncol 2008, 26(17):2795-99.
Bonnet and Dick, "Human acute myeloid leukemia is organized as a hierarchy that originates from a primitive hematopoietic cell," 1997, 3(7):730-737.
Bonnet, "Normal and leukaemic stem cells", Br J Haematol, (2005), 130(4):469-479.
Borovski, "Cancer stem cell niche: the place to be," Cancer Res 2011, 71(3):634-639.
Bostonbiomedical.com, "Boston Biomedical Data at ASCO 2015 Highlights Potential of Novel Investigational Cancer Stem Cell Pathway Inhibitors BBI608 and BBI503 in Multiple Cancer Types", retrieved on [Jun. 1, 2015] retrieved from URL<http://www.bostonbiomedical.com/boston-biomedical-data-at-asco-2015-highlights-potential-of-novel-investigationsal-cancer-stem-cell-pathway-inhibitors-bbi608-and-bbi-503-in-multiple-cancer-types/>, 4 pages.
Braatz, "Crystallization: Particle Size Control," Encyclopedia of Pharmaceutical Technology, Swarbrick, ed. New York: Informa Healthcare, Third Edition, 2007, 858-871.
Bromberg, "Stat3 as an Oncogene," Cell, 1999, 98(3):295-303.
Bromberg, J., "Stat proteins and oncogenesis," J Clin Invest, 2002, 109(9):1139-1142.
Buettner et al., "Activated STAT signaling in human tumors provides novel molecular targets for therapeutic intervention," Clinical Cancer Research, 2002, 8(4): 945-954.
Burdelya, "Stat3 Activity in Melanoma Cells Affects Migration of Immune Effector Cells and Nitric Oxide-Mediated Antitumor Effects," J Immunol, 174(7):3925-31.
Burke, WM, et al., "Inhibition of Constitutively Active STAT-3 Suppresses Growth of Human Ovarian and Breast Cancer Cells", Oncogene, Nov. 29, 2001, 20(55):7925-7934.
Byrn, "Solid-State Chemistry of Drugs, 2d, Chapter 11 Hydrates and Solvates/Hydrates," 233-247.
Cains, "Classical Methods of Preparation of Polymorphs and Alternative Sold Forms," Polymorphism in Pharmaceutical Solids, 2nd Edition, 2009, 70 pages.
Caira, "Crystalline Polymorphism of Oeganic Compounds, Topics in Chemistry," 1998, 198:163-208.
Campbell, "Cytokine-Mediated Inflammation, Tumorigenesis, and Disease Associated JAKISTA/SOCS Signaling Circuits in the CNS," Brain Res Brain Res Rev, 2005, 48(2):166-77.
Capsugel, "Technical Reference File: Hard Gelatin Capsules," 4th Edition, 57 pages.
Carson, "Interferon-Alpha-Induced Activation of Signal Transducer and Activator of Transcription Proteins in Malignant Melanoma," Clin Cancer Res, 1998,4(9):2219-2228.
Catlett-Falcone et al. "Constitutive Activation of Stat3 Signaling Confers Resistance to Apoptosis in Human U266 Myeloma Cells," Immunity, 1999, 10(1):105-115.
Cesari, "Inflammatory Markers and Onset of Cardiovascular Events: Results from the Health ABC Study," Circulation, 2003 108(19):2317-2322.
Chan et al., "Disruption of Stat3 reveals a critical role in both the initiation and the promotion stages of epithelial carcinogenesis," J. Clin. Invest., 2004, 114:720-728.
Chang et al., "Activation of STAT3 in thymic epithelial tumours correlates with tumour type and clinical behavior," J Pathol, 2006, 210(2):224-233.
Chang et al., "Evaluation of Tumor Cell-Tumor Microenvironment Component Interactions as Potential Predictors of Patient Response to Napabucasin," Mol Can Res., Jul. 1, 2019, 13(7):1429-1434.
Chen et al., "Signal transducer and activator of transcription 3 is involved in cell growth and survival of human rhabdomyosarcoma and osteosarcoma cells," BMC Cancer, 2007, 7:111.
Chen et al., "Constituents of Markhamia Hildebrandtii (Baker) Sprague and their Antitumor Activity", STN Database Accession No. 1986:568912,Chemical Abstracts Service, Columbus, OH XP002662423, Nov. 15, 1986, 2 pgs.
Chen et al., "Stat3 activation in human endometrial and cervical cancers," Br J Cancer., 2007, 96(4):591-599.
Cho-Vega et al., "Suppressor of cytokine signaling 3 expression in anaplastic large cell lymphoma," Leukemia, 2004 18(11):1872-1878.
Clarke, "Self-renewal and solid-tumor stem cells," Biol Blood Marrow Transplant, Feb. 2005, 11(2 suppl 2):14-16.
Clarke, "Cancer Stem Cells—Perspectives on Current Status and Future Directions: AACR Workshop on Cancer Stem Cells," Cancer Research, 2006, 66(19):9339-44.
Clinicaltrials.com, "A Study of BBI603 Administered With Paclitaxel in Adult Patients With Advanced Malignancies", ID NCT01325441, Boston Biomedical, [retrieved on Feb. 19, 2016] Retrieved from URL <http://clinicaltrials.gov/archive/ NCTO 1325441/2011_03_28>, 3 pages.
Clinicaltrials.com, "A Study of BBI608 in Adult Patients with Advanced, Refractory Hematologic Malignancies," ID NCT02352558, Boston Biomedical, [retrieved on Feb. 19, 2016] Retrieved from URL <https://clinicaltrials.gov/ct2/show/NCT02352558?term-BBI608 &rank-1>, 5 pages.
Clinicaltrials.com, "A Study of BBI608 in Adult Patients with Advanced Colorectal Cancer," ID NCT01776307, [retrieved Aug. 22, 2019] retrieved from URL <https://clinicaltrials.gov/ct2/show/NCT01776307>, 10 pages.
Clinicaltrials.com, "A Study of BBI608 in Combination with Standard Chemotherapies in Adult Patients with Advanced Gastrointestinal Cancer," ID NCT02024607, Boston Biomedical, [retrieved on Feb. 19, 2016] Retrieved from URL <https://clinicaltrials.gov/ct2/show/NCT02024607?term=bbi608&rank=3>, 7 pages.
Clinicaltrials.com, "A Study of BBI608 in Combination with Temozolomide in Adult Patients with Recurrent or progressed Glioblastoma," ID NCT02315534, [retrieved on Feb. 19, 2016] Retrieved from URL <https://clinicaltrials.gov/ct2/show/NCT02315534? term=BBI608&rank=10.
Clinicaltrials.com, "A Study of BBI608 in Combination with Standard Chemotherapies in Adult Patients with Pancreatic Cancer," ID NCT02231723, [retrieved Mar. 19, 2019] Retrieved from URL <https://clinicaltrials.gov/ct2/show/NCT02231723>, 15 pages.
Clinicaltrials.com, "A Study of BBI608 Administered in Combination With Immune Checkpoint Inhibitors in Adult Patients With Advanced Cancers," Id NCT02467361, [retrieved Aug. 16, 2019] Retrieved from URL <https://clinicaltrials.gov/ct2/show/NCT02467361>, 9 pages.
Collins, "Prospective Identification of Tumorigenic Prostate Cancer Stem Cells," Cancer Res, 2005, 65(23):10946-10951.
Colman et al., "Effect of a small molecule inhibitor of the JAK2/STAT3 pathway on self-renewal of glioblastoma stem cells," Journal of Clinical Oncology, 2008, 26:15S.
Colman de Saizarbitoria et al., "Bioactive furonaphtoquinones from Tabebuia barbata (Bignoniaceae)," Acta Cient Venez, 1997, 48(1):42-46.
Corvinus et al., "Persistent STAT3 activation in colon cancer is associated with enhanced cell proliferation and tumor growth," Neoplasia, 2005, 7(6):545-555.
Dalerba, "Phenotypic Characterization of Human Colorectal Cancer Stem Cells," Proc Natl Acad Sci USA, Jun. 2007, 104(24):10158-10163.
Danishefsky et al., "Stereospecific total syntheses of dl-coriolin and dl-coriolin B," J of Am Chem Soc., 1981, 103(12):3460-3467.
Darnell et al., "Validating Stat3 in cancer therapy", Nature Medicine, Jun. 2005, 11(6):595-596.
De Araujo et al. "STAT3 expression in salivary gland tumours," Oral Oneal., 2008, 44(5):439-45.
De Boer, "Liposomal doxorubicin in metastatic breast cancer," Breast Cancer Res., 1999, 2:66629-66631.

(56) References Cited

OTHER PUBLICATIONS

Dean et al., "Tumour Stem Cells and Orig Resistance", Nat Rev Cancer, 2005, 5:275-284.

"Definition of Cancer", MedicineNet.com., [Online] retrieved from the internet: <http://www.medterms.com>, (2004).

Defant et al., "Regioselectivity in the Multi-Component Synthesis of Indolizinoquinoline-5,12-dione Derivatives," European Journal of Organic Chemistry, Sep. 2006, 18:4201-4210.

Desmond et al., "The Synthetic Furanonaphthoquinone Induces Growth Arrest, Apoptosis and Differentiation in a Variety of Leukaemias and Multiple Myeloma Cells." Brit. J. Haematol., 2005, 131(4):520-529.

Diaz et al., "Furanonaphthoquinones from *Tabebuia ochracea* ssp. *neochrysanta*", J. Nat. Prod., 1996, 59(4):423-424.

Diaz et al., "Activation of stat3 in primary tumors from high-risk breast cancer patients is associated with elevated levels of activated SRC and survivin expression," Clin Cancer Research, 2006, 12(1):20-8.

Dien et al., "Signal Transducers and Activators of Transcription-3 Up-Regulates Tissue Inhibitor of Metalloproteinase-1 Expression and Decreases Invasiveness of Breast Cancer," Am J of Pathology., 2006, 169(2):633-642.

Doyle and Ross, "Multidrug Resistance Mediated by the Breast Cancer Resistance Protein BCRP (ABCG2)", Oncogene, 2003, 22(47):7340-7358.

Elzagheid, Adam, et al., "Nuclear [beta]-catenin expression as a prognostic factor in advanced colorectal carcinoma", World Journal of Gastroenterology, Jun. 28, 2008, 14(24):3866-3871.

Epling-Burnette et al., "Inhibition of STAT3 signaling leads to apoptosis of leukemic large granular lymphocytes and decreased Mcl-1 expression," J. Clin. Invest., 2001, 107(3):351-362.

Eyler, "Survival of the Fittest: Cancer Stem Cells in Therapeutic Resistance and Angiogenesis", J. Clin. Oneal., 2008, 26(17):2839-2845.

Eyong, et al., "Semisynthesis and antitumoral activity of 2-acetylfuranonaphthoquinone and other naphthoquinone derivatives from lapachol", Bioorganic & Medicinal Chemistry Letters, 2008, 18(20):5387-5390.

Fagerholm, "Experimental Estimation of the Effective Unstirred Water Layer Thickness in the Human Jejunum, and its Importance in Oral Drug Absorption," Eur. J. Pharm. 1995, 3:247-253.

Faloppi et al., "The correlation between LDH serum levels and clinical outcome in advanced biliary tract cancer patients treated with first line chemotherapy," Scientific Reports, 2016, 6:24136.

Farina, F., et al., "La Reaccion De La 2-Acetil-1.4-Benzoouinona V Ouinonas Analogas Con Tioles. Aplicacion a La Sintesis De Tiofenouinonas", Analesde Quimica, 1976, (72):902-908.

Feldmann, M, "Role of Cytokines in Rheumatoid Arthritis", Annu Rev Immunol, 1996, 14:397-440.

Fotsing, "Identification of an Anti-Inflammatory Principle from the Stem Bark of Millettia Versicolor," Planta Med, Aug. 1, 2003, 69(8):767-70.

Frank, "ABCB5-Mediated Doxorubicin Transport and Chemoresistance in Human Malignant Melanoma," Cancer Res, 2005, 65(10):4320-4333.

Frank, "STAT3 as a Central Mediator of Neoplastic Cellular Transformations," Cancer Left., 2007, 251(2):199-210.

Fu, "STAT3 in Immune Responses and Inflammatory Bowel Disease," Cell Res, 16(2):214-219(2006).

Furqan, et al., "STAT inhibitors for cancer therapy," J Hematology & Oncology, 2013, 6:90.

Furtek et al., "Strategies and Approaches of Targeting STAT3 for Cancer Treatment," ACS Chem. Biol., Jan. 5, 2016, 11(2):308-318.

Gafner, "Antifungal and Antibacterial Naphthoquinones from Newbouldia Laevis Roots," Phytochemistry., 2007,42(5):1315-1320.

Gao et al., "Inhibition of STAT3 expression by siRNA suppresses growth and induces apoptosis in laryngeal cancer cells," Acta Pharmacol Sin., 2005, 26(3):377-383.

Gao et al., "Knockdown of Stat3 expression using RNAi inhibits growth of laryngeal tumors in vivo," Acta Pharmacol Sin., 2006, 27(3):347-352.

Gao et al., "Constitutive activation of JAK-STAT3 signaling by BRCA1 in human prostate cancer cells," FEBS Letters, 2001, 488(3):179-184.

Garcia et al., "Constitutive activation of Stat3 in fibroblasts transformed by diverse oncoproteins and in breast carcinoma cells," Cell Growth Differ, 1997, 8(12):1267-1276.

Garcia, "Constitutive activation of Stat3 by the Src and JAK tyrosine kinases participates in growth regulation of human breast carcinoma cells", Oncogene, 2001, 20:2499-2513.

General Correspondence from Boston Biomedical to Department of Health and Human Services Investigational New Drug Application, Napabucasin, IND 100887, Serial No. 0179, Dec. 22, 2017, 8 pages.

Goodell, "Isolation and Functional Properties of Murine Hematopoietic Stem Cells That are Replicating in Vivo," J. Exp. Med. 183. 4(1996):1797-1806.

Gormann, "Furanonaphthoquinones, Atraric Acid and a Benzofuran from the Stem Barks of Newbouldia Laevis," Phytochemistry, 64.2(2004):583-587.

Gowrishankar et al., "Inducible but Not Constitutive Expression of PD-L1 in Human Melanoma Cells Is Dependent on Activation of NF-κB," Plos One., Apr. 6, 2015, pp. 1-19.

Grandis et al., "STAT signaling in head and neck cancer," Oncogene, 2000, 19(21):2489-2495.

Gritsko et al. "Persistent activation of stat3 signaling induces survivin gene expression and confers resistance to apoptosis in human breast cancer cells," Clinical Cancer Research Center, 2006, 12(1):11-19.

Gupta, et al., "Cancer stem cells: mirage or reality?" Nat Med, Sep. 2009, 15(9):1010-1012.

Hagiwara, et al., "Domino Michael-O-alkylation reaction: one-pot synthesis of 2,4-diacylhydrofuran derivatives and its application to antitumor naphthofuran synthesis", J. Chem. Soc., Perkin Trans., 2001, 22:2946-2957.

Hagiwara, et al., "Tandem nucleophilic reaction leading to hydrofurans: application to one-pot synthesis of antitumor naphthofuran natural product", HETEROCYCLES, 1999, (51)3:497-500.

Hagler et al., "Sophorolipids Decrease IgE Production in U266 Cells by Downregulation of BSAP (Pax5), TLR-2, STAT3 and IL-6," J Allergy Clin Immunol, 119(1):S263.

Haleblian, "Pharmaceutical Applications of Polymorphism," J. Pharm. Sci. Aug. 1969, 58(8):911-29.

Hambardzumyan, "Radiation Resistance and Stem-Like Cells in Brain Tumors," Cancer Cell, 2006, 10(6):454-456.

Han Li, "Unusual Naphthoquinone Derivatives from the Twigs of Avicennia Marina," J. Nat. Prod., 2007, 70:923-927.

Harada, T, "Increased Expression of STAT3 in SLE T Cells Contributes to Enhanced Chemokine-Mediated Cell Migration", Autoimmunity, 2006, 40:1-8.

Haraguchi, "Characterization of a Side Population of Cancer Cells from Human Gastrointestinal System," Stem Cells, 2006, 24(3):506-513.

Harris, "Cutting Edge: An in Vivo Requirements for STAT3 Signaling in TH17 Development and TH17-dependent Autoimmunity," J Immunol, 179(7):4313-4317.

Hart, H, "Organic Chemistry: A Short Course", Houghton Mifflin Harcourt College Division, Boston, Massachusetts, 9th Edition, 1995, 279.

Haura et al., "Activated epidermal growth factor receptor-Stat-3 signaling promotes tumor survival in vivo in non-small cell lung cancer," Clin Cancer Res, 2005, 11(23):8288-8294.

He et al., "Prodrugs of Phosphonates, Phosphinates, and Phosphates," Prodrugs, 2007, pp. 224-264.

Hirai et al., "Furanonaphthoquinone derivatives as antiviral, antifungal and antibacterial agents," STN Database Accession No. 1997:632811, 1 pg.

Hirai, "Furanonaphthoquinone Analogs Possessing Preferential Antitumor Activity Compared to Normal Cells," Cancer Detection and Prevention, 1999 23(6):539-550.

(56) References Cited

OTHER PUBLICATIONS

Hironaka, Shuichi, et al., "Weekly paclitaxel as second-line chemotherapy for advanced or recurrent gastric cancer", Gastric Cancer, Springer-Verlag, TO, vol. 9, No. 1, (Feb. 1, 2006), 14-18.
Ho, "Side Population in Human Lung Cancer Cell Line and Tumors is Enriched with Stem-Like Cancer Cells," Cancer Res., 2007, 67(10):4827-4833.
Holtick et al., "STAT3 is essential for Hodgkin lymphoma cell proliferation and is a target of tyrphostin AG17 which confers sensitization for apoptosis," Leukemia., 2005, 19 (6):936-944.
Horiguchi et al., "Activation of signal transducer and activator of transcription 3 in renal cell carcinoma: a study of incidence and its association with pathological features and clinical outcome," The Journal of Urology, 2002, 168(2):762-765.
Hsiao et al., "Constitutive activation of STAT3 and STAT5 is present in the majority of nasopharyngeal carcinoma and correlates with better prognosis," Br J Cancer., 2003, 89(2):344-349.
Huang, M., et al., "Constitutive Activation of Stat 3 Oncogene Product in Human Ovarian Carcinoma Cells", Gynecologic Oncology, 2000, 79(1):67-73.
Hubbard et al., "Napabucasin: An Update on the First-in-Class Cancer Sternness Inhibitor," Drugs, Jul. 2017, 77(10):1091-1103.
Igawa et al., "Efficacy of chemotherapy with carboplatin and paclitaxel for unresectable thymic carcinoma," Lung Cancer, Feb. 2010, 67(2):194-197.
Ikegawa et al., "Furonaphthoquinone derivatives as antiviral, antifungal and antibacterial agents," STN Database Accession No. 1989:560194, 2 pages.
Inagaki et al., "Synthesis and Cytotoxicity on Human Leukemia Cells of Furonaphthoquinones Isolated from Tabebuia Plants," Chemical and Pharmaceutical Bulletin, 61(6):670-673.
International Search Report and Written Opinion in International Application No. PCT/US2008/075848, dated May 14, 2009, 8 pages.
International Search Report and Written Opinion in International Application No. PCT/US2008/075906, dated Dec. 8, 2008, 10 pages.
International Search Report and Written Opinion in International Application No. PCT/US2016/028179, dated Oct. 20, 2016, 11 pages.
International Search report and Written Opinion in International Application No. PCT/US2017/014163, dated Jul. 10, 2017, 13 pages.
International Search Report and Written Opinion in International Application No. PCT/US2008/075903, dated Feb. 24, 2009, 12 pages.
International Search Report and Written Opinion in International Application No. PCT/US2011/029281, dated Aug. 12, 2011, 10 pages.
International Search Report and Written Opinion in International Application No. PCT/US2011/029283, dated May 17, 2011, 8 pages.
International Search Report and Written Opinion in International Application No. PCT/US2014/033566, dated Dec. 16, 2014, 18 pages.
International Search Report and Written Opinion in International Application No. PCT/US2016/028177, dated Jul. 20, 2016, 10 pages.
International Search Report and Written Opinion in International Application No. PCT/US2016/028178, dated Aug. 9, 2016, 12 page.
International Search Report and Written Opinion in International Application No. PCT/US2018/032937, dated Aug. 24, 2018, 11 pages.
International Search Report and Written Opinion in International Application No. PCT/US2017/063734, dated Jan. 25, 2018, 13 pages.
International Search Report and Written Opinion in International Application No. PCT/IB2017/001573, dated May 16, 2018, 16 pages.
International Search Report and Written Opinion in International Application No. PCT/US2018/023827, dated Aug. 20, 2018, 20 pages.
International Search Report and Written Opinion in International Application No. PCT/US2019/034658, dated Sep. 10, 2019, 15 pages.
Ishihara and Hirano, "IL-6 in Autoimmune Disease and Chronic Inflammatory Proliferative Disease," Cytokine Growth Factor Rev, 2002, 13(4-5):357-368.
International Preliminary Report on Patentability in International Application No. PCT/US2008/075906, dated Mar. 16, 2010, 10 pages.
International Preliminary Report on Patentability in Application No. PCT/US2016/028179, dated Oct. 17, 2017, 8 pages.
International Preliminary Report on Patentability in International Application No. PCT/US2017/014163, dated Jul. 24, 2018, 8 pages.
International Preliminary Report on Patentability in International Application No. PCT/US2008/075903, dated Mar. 16, 2010, 11 pages.
International Preliminary Report on Patentability in International Application Serial No. PCT/US2011/029281, dated Sep. 25, 2012, 7 pages.
International Preliminary Report on Patentability in International Application No. PCT/US2011/029283, dated Sep. 25, 2012, 6 pages.
International Preliminary Report on Patentability in International Application No. PCT/US2014/033566, dated Oct. 13, 2015, 13 pages.
International Preliminary Report on Patentability in International Application No. PCT/US2016/028177, dated Oct. 17, 2017, 7 pages.
International Preliminary Report on Patentability in International Application No. PCT/US2016/028178, dated Oct. 17, 2017, 8 pages.
International Preliminary Report on Patentability in International Application No. PCT/US2017/063734, dated Jun. 4, 2019, 8 pages.
International Preliminary Report on Patentability in International Application No. PCT/IB2017/001573, dated May 28, 2019, 10 pages.
International Preliminary Report on Patentability in Application No. PCT/US2008/075848, dated Mar. 16, 2010, 6 pgs.
International Preliminary Report on Patentability in Application No. PCT/US2018/023827, dated Oct. 1, 2019, 13 pages.
International Preliminary Report on Patentability in Application No. PCT/US2018/032937, dated Nov. 19, 2019, 9 pages.
Invitation to Pay Additional Fees and, Where Applicable, Protest Fee in International Application No. PCT/IB2017/001573, dated Mar. 13, 2018, 15 pages.
Invitation to Pay Additional Fees and, Where Applicable, Protest Fee in International Application No. PCT/US2018/023827, dated Jun. 18, 2018, 15 pages.
Itoh et al., "Requirement of STAT3 activation for maximal collagenase-1 (MMP-1) induction by epidermal growth factor and malignant characteristics in T24 bladder cancer cells," Oncogene, 2006, 25(8):1195-1204.
Itoigawa, "Cancer Chemopreventive Activity of Naphthoquinones and Their Analogs from Avicennia Plants," Cancer Letters, 2001, 174(2):135-139.
Ivashkiv and Tassiulas, "Can SOCS make Arthritis Better?," J Clin Invest, 2003, 111(6):795-797.
Iwamaru et al., "A novel inhibitor of the STAT3 pathway induces apoptosis in malignant glioma cells both in vitro and in vivo," Oncogene, 2007, 26(17):2435-44.
Ji et al., "Clinicopathological implications of NQO1 overexpression in the prognosis of pancreatic adenocarcinoma," Oncol Lett., Mar. 7, 2017, 13(5):2996-3002.
Johnson et al., "Abrogation of Signal Transducer and Activator of Transcription 3 Reactivation After Src Kinase Inhibition Results in Synergistic Antitumor Effects." Clin. Cancer Res. 13.14(2007):4233-4244.
Johnston et al. "STAT3 Signaling: Anticancer Strategies and Challenges." Mol. Interv. 11.1(2011):18-26.

(56) References Cited

OTHER PUBLICATIONS

Jones, "Cancer Stem Cells: Are We Missing the Target?," J Natl Cancer Inst, 2004, 96(8):583-585.
Jonker et al., "Napabucasin versus placebo in refractory advanced colorectal cancer: a randomized phase 3 trial." Lancet Gastroenterol Hepatol., Apr. 2018 2018, 3(4):263-270.
Jordan, "Cancer stem cells," N Engl J Med., Sep. 21, 2006, 355(12):1253-1261.
Kamel-Reid et al., "Engraftment of immune-deficient mice with human hematopoietic stem cells," Science, Dec. 23, 1988, 242:1706-1709.
Kanda et al., "STAT3 is constitutively activated and supports cell survival in association with survivin expression in gastric cancer cells," Oncogene, 2004, 23(28):4921-4929.
Kang, "A New Route to Naphtho[2,3-b]furan-4,9-Diones from Thia-Substituted 1,4-Naphthoquinones," J. Chem. Soc. Perkin Trans., 1990, 441-445.
Katoh et al., "STAT3-Induced WNT5A Signaling Loop in Embryonic Stem Cells, Adult Normal Tissues, Chronic Persistent Inflammation, Rheumatoid Arthritis and Cancer," Int. J. Mol. Med., 2007, 19(2):273-278.
Kijima et al., "STAT3 activation abrogates growth factor dependence and contributes to head and neck squamous cell carcinoma tumor growth in vivo," Cell Growth Diff., 2002, 13:355-362.
Kikuchi, T., et al., "Electrophotographic Photosensitive Member", STN Database Accession No. 1992:245248, Chemical Abstracts Service, Columbus, OH XP002661424, (Jun. 13, 1992), 5 DOS.
Kim et al., "A specific STAT3-binding peptide exerts antiproliferative effects and antitumor activity by inhibiting STAT3 phosphoiylation and signaling," Cancer Res., Apr. 15, 2014, 74(8):2144-2151.
Kim et al., "Inhibition of Signal Transducer and Activator of Transcription 3 Activity Results in Down-Regulation of Survivin Following Irradiation," Mol. Cancer Thera. 2006, 5(11):2659-2665.
Kim, "JAK-STAt Signaling Mediates Gangliosides-lnduced Inflammatory Responses in Brain Microglial Cells," J Biol Chem, 2002, 277(43):40594-40601.
Klein et al., "Increased Expression of Stem Cell Markers in Malignant Melanoma", Mod Pathol., 2007, 20:102-107.
Kobayashi et al., "One-Pot Synthesis of Naphtho[2,3-b]fiiran-4,9-diones by Sequential Coupling/Ring Closure Reactions", Tetrahedron Letters, 1997, 38(5):837-840.
Kobayashi et al., "An Improved Method for the Preparation of 4,7-Dioxo-4,7-dihydrobenzo[b]thiophene-2-carboxylates from 2-Acyl-1,4-benzoquinones and Mercaptoacetates,", Heterocyclesm, 2001, 55(21):2423-2429.
Kondo, "Persistence of a Small Subscription of Cancer Stem-Like Cells in the C6 Glioma Cell Line," Proc Natl Acad Sci USA, 2004, 101(3):781-786.
Konnikova et al., "Knockdown of STAT3 expression by RNAi induces apoptosis in astrocytoma cells," BMC Center 2003, 3:23.
Kortylewski, M, et al., "Inhibiting STAT3 Signaling in the Hematopoietic System Elicits Multicomponent Antitumor Immunity", Nat Med, 11(12):1314-1321.
Koyanagi, "A Facile Synthesis of 2-Acteylnaphtho[2,3-b]furan-4,9-Dione," Journal of Heterocyclic Chemistry, 1995, 32:1289-1291.
Koyanagi, "A New Synthetic of 2-SubstitutedNaphtho[2,3-b]furan-4,9-Dione," Journal of Heterocyclic Chemistry, 1997, 34:407-412.
Koyama et al., "Micellar Electrokinetic Chromatography (MEKC) Separation of Furanonaphthoquinones from Tabebuia hnpetiginosa," Chem. Pharm. Bull. (Tokyo), Jun. 2000, 48(6):873-875.
Krause, "Rheumatoid Arthritis Synoviocyte Survival is Dependent on Stat3," J Immunol, 2002, 169(11):6610-6.
Kumar, "Clinical Trials and Progress with Paclitaxel in Ovarian Cancer," International Journal of Women's Health 2010, 2:411-427.
Kusaba et al., "Expression of p-STAT3 in human colorectal adenocarcinoma and adenoma; correlation with clinicopathological factors," Journal of Clinical Pathology, 2005, 58(8):833-838.
Laatsch, "Synthese von Maritinon und anderen 8,8'-Bijuglonen," Liebigs Annalen der Chemie, 1985, 12:2420-2442 English Abstract.
Lai et al., "STAT3 is activated in a subset of the Ewing sarcoma family of tumours," J Pathol. 2006, 208(5):624-632.
Lai, "Signal Transducer and Activator of Transcription-3 Activation Contributes to High Tissue Inhibitor of Metalloproteinase-1 Expression in Anaplastic Lymphoma Kinase-Positive Anaplastic Large Cell Lymphoma," Am J Pathol, 2004, 164(6):2251-58.
Lande, "The Relationship Between Membrane Fluidity and Permeabilities to Water, Solutes, Ammonia, and Protons," J. Gen. Physiol, 1995, 106:67-84.
Larochelle et al., "Identification of primitive human hematopoietic cells capable of repopulating NOD/SCID mouse bone marrow: implications for gene therapy," Nat. Med., Dec. 1996, 2:1329-1337.
Lassman et al., "STAT3 mRNA and protein expression in colorectal cancer: effects on STAT3-inducible targets linked to cell survival and proliferation," J Clin Pathol. 2007, 60(2):173-9.
Lau et al., "Inhibition of Stat3 activity by YC-1 enhances chemosensitivity in hepatocellular carcinoma," Cancer Biol Ther., 2007, 6(12):1900-7.
Le et al., "PD-1 Blockade in Tumors with Mismatch-Repair Deficiency," N. Engl. J. Med., Jun. 25, 2015, 372:2509-2520.
Lee, et al., "Ceric Ammonium Nitrate (CAN)-Mediated Oxidative Cycloaddition of 1,3-Dicarbonyls to Conjugated Compounds. Efficient Synthesis of Dihydrofurans, Dihydrofurocoumarins, Dihydrofuroquinolinones, Dihydrofurophenalenones, and Furonaphthoquinone Natural Products", Tetrahedron, 2000, 56(45):8845-8853.
Lee, "Efficient Synthesis of Cytotoxic Furonaphthoquinone Natural Products," Synthetic Communications, 2001, 31(3):381-386.
Leong et al., Targeted inhibition of Stat3 with a decoy oligonucleotide abrogates head and neck cancer cell growth Proc Natl Acad Sci USA, 2003, 100(7):4138-43.
Li et al., "Abstract LB-253: Inhibition of Sternness by BBI608 is Sufficient to Suppress Cancer Relapse and Metastasis", Cancer Research. AACR 106th Annual Meeting 2015, Apr. 18-22, 2015, Philadelphia, PA, published Aug. 1, 2015, 75(15 Supplement).
Li et al., "Autocrine-mediated activation of STAT3 correlates with cell proliferation in breast carcinoma lines," J. Biol. Chem. 2002, 277:17397-17405.
Li et al., "Inhibition of growth and metastasis of human hepatocellular carcinoma by antisense oligonucleotide targeting signal transducer and activator of transcription 3," Clin Cancer Res., 2006, 12(23):7140-8.
Li, "Identification of Pancreatic Cancer Stem Cells," Cancer Res, 2007, 67(3):1030-1037.
Li et al., "Feedback activation of STAT3 mediates trastuzumab restistance via upregulation of MUC1 and MUC4 expression," OncoTarget, Jun. 26, 2014, 5(18):8317-8329.
Li et al., "Suppression of cancer relapse and metastasis by inhibiting cancer stemness", Proceedings of the National Academy of Sciences, Jan. 20, 2015, 112(6):1839-1844.
Libby et al., "Inflammation and Atherosclerosis," Circulation, 2002, 105(9):1135-1143.
Lim, "Stat3 Contributes to Keloid Pathogenesis via Promoting Collagen Production, Cell Proliferation and Migration," Oncogene, 2006, 25(39):5416-5425.
Lin, L, et al., "STAT3 is Necessary for Proliferation and Survival in Colon Cancer-Initiating Cells", Cancer Res, 71(23):7226-7237.
Lin et al., "STAT signaling in the pathogenesis and treatment of leukemias," Onconogene, May 15, 2000, 19(21):2496-2504.
Lin et al., "Constitutive activation of JAK3/STAT3 in colon carcinoma tumors and cell lines: inhibition of JAK3/STAT3 signaling induces apoptosis and cell cycle arrest of colon carcinoma cells," Am J Pathol, 2005, 167:969-980.
Lin et al., "Significance of the expression of phosphorylated signal transducer and activator of transcriplion-3, -Akt, and -cyclin D1 in angiosarcoma," J. Derm. Sci., 2007, 48(1):64-66.
Lin et al., "Significance of the expression of phosphorylated-STAT3, -Akt, and -ERK1/2 in several tumors of the epidermis," J. Derm. Sci., 2007, 48(1):71-73.
Ling, "Mesenchymal Stem Cells Overexpressing IFN-Inhibit Breast Cancer Growth and Metastases through Stat3 Signaling in a Syngeneic Tumor Model," Cancer Microenviron, 2010, 3(1):83-95.

(56) References Cited

OTHER PUBLICATIONS

Liou et al., "Reactive oxygen species in cancer," Free Radic Res., May 2010, 44(5):479-496.
Lipinski, "Experimental and Computational Approaches to Estimate Solubility and Permeability in Drug Discovery and Development Settings," Adv. Drug Deliv. Rev., 2001, 46(1-3):3-26.
Liu et al., "Enantio- and Diastereoselective Intermolecular Stetter Reaction of Glyoxamide and Alkylidene Ketoamides," Organic Letters., 2009, 11(13):2856-2859.
Liu et al., "Expression and clinical significance of COX-2, p-Stat3, and p-Stat5 in esophageal carcinoma," Ai Zheng, 2007,26(5):458-62 [English Abstract].
Lobo et al., "The biology of cancer stem cells," Annu Rev Cel Cev Biol., 2007, 23:675-699.
Lopes et al., "Synthesis of Dimethoxyfuranonaftoquinones," Synthetic Communications, Oct. 1, 1988, 18(14):1731-1742.
Lopes, "Efficient Synthesis of Cytotoxic Quinones: 2-Acetyl-4H,9H-naphtho[2,3-b]furan-4, 9-Dione (6) and (:t)-2-(1-Hydroxyethyl)-4H,9H-naphtho[2,3-b]furan-4,9-Dione (7)," Journal of Heterocyclic Chemistry, 1984, 21:621-622.
Lovato, "Constitutive STAT3 Activation in Intestinal T Cells from Patients with Crohn's Disease," J Biol Chem, 2003, 278(19):16777-16781.
Ma et al., "Constitutive activation of Stat3 signaling pathway in human colorectal carcinoma," World J. Gastroent., 2004, 10(11):1569-1573.
Ma, "Identification and Characteristic of Tumorigenic Liver Cancer Stem/Progenitor Cells," Gastroenterology, 2007, 132(7):2542-2556.
Manolagas, "Role of Cytokines in Bone Resorption," Bone, 1995, 17(2 Suppl):63S-67S.
Maruyama, A., et al., "Electrophotographic Photoreceptor, Process Cartridge and Electrophotographic Apparatus Using Same", STN Database Accession No. 1999:157137 Chemical Abstracts Service, Columbus, OH XP002661425, (Mar. 10, 1999), 3 pgs.
Masayuki et al., "Cytotoxic Activity toward KB Cells of 2-Substituted Naphtho[2,3-b]furan-4,9-Diones and Their Related Compounds," Biosci. Biotechnol. Biochem., 2006, 70(4):1009-1012.
Masuda et al., "Constitutive activation of signal transducers and activators of transcription 3 correlates with cyclin D1 overexpression and may provide a novel prognostic marker in head and neck squamous cell carcinoma," Cancer Res. (2002), 62(12):3351-5.
Matsumoto et al., "Individual Formulations Nature and Preparation Method," Medicine Manual, Mar. 20, 1989, 1st Edition:80, translation 5 pages.
McCune et al., "The SCID-hu mouse: murine model for the analysis of human hematolymphoid differentiation and function," Science, Sep. 23, 1988, 241:1632-1639.
Migone, T.-S., et al., "Constitutively Activated Jak-STAT Pathway in T Cells Transformed With HTLV-I", Science, Jul. 7, 1995, 269(5220):79-81.
Ministry of Health of the Russian Federation, "Guidelines: For the Experimental(Preclinical) Investigation of New Pharmaceutical Substances," Moscow, 2000, p. 111.
Mizoguchi et al., Journal of Neuropathology and Experimental Neurology, 2006, 65(12):1181-1188.
Mora et al., "Constitutive activation of Stat3 in human prostate tumors and cell lines: direct inhibition of Stat3 signaling induces apoptosis of prostate cancer cells," Cancer Res, 2002 62(22):6659-6666.
Morikawa et al., "STAT3 Expression, Molecular Features, Inflammation Patterns, and Prognosis in a Database of 724 Colorectal Cancers," Clinical Cancer Research, Mar. 15, 2011, 17(6):1452-1462.
Morrissette, "High-Throughput Crystallization: Polymorphs, Salts, Co-Crystals and Solvates of Pharmaceutical Solids," Adv. Drug Delivery Rev. 2004, 56:275-300.
Muller et al., "Potential antipsoriatic agents: lapacho compounds as potent inhibitors of HaCaT cell growth," J. Nat. Prod., 1999, 62:1134-1136.
Naciuk et al., "Exploitation of a tuned oxidation with N-haloimides in the synthesis of caulibugulones A-D," J Org Chem., May 17, 2013, 78(10):5026-5030.
Nielsen et al., "Inhibition of constitutively activated Stat3 correlates with altered Bcl-2/Bax expression and induction of apoptosis in mycosis fungoides tumor cells," Leukemia, 1999, 13(5):735-738.
Ning et al., "Signal transducer and activator of transcription 3 activation is required for Asp(816) mutant c-Kit-mediated cytokine-independent survival and proliferation in human leukemia cells," Blood, 2001, 97:3559-3567.
Nishi et al., "Retrospective analysis of the international standard-dose FOLFIRI (plus bevacizumab) regimen in Japanese patients with unresectable advanced or recurrent colorectal carcinoma," International Journal of Clinical Oncology, Oct. 2011, 16(5):488-493.
Niu et al., "Gene therapy with dominant-negative Stat3 suppresses growth of the murine melanoma B16 tumor in vivo," Cancer Res., 1999, 15;59(20):5059-5063.
Niu et al., "Roles of activated Src and Stat3 signaling in melanoma tumor cell growth," Oncogene, 2002, 21(46):7001-7010.
Niu et al., "Constitutive Stat3 activity up-regulates VEGF expression and tumor angiogenesis,"Oncogene, 2002, 21(13):2000-2008.
No Author, "International Research Congress on Natural Product as Medicinal Agents", Strasbourg—France, July 6-11, Planta Med, Jul. 1980, 39(3):194-196.
Oettle et al., "Paclitaxel as weekly second-line therapy in patients with advanced pancreatic carcinoma," Anticancer Drugs, 2000, 11(8):635-638.
Oh et al., "Implications of NQ01 in cancer therapy," BMB Reports, Nov. 30, 2015, 48(11):609-617.
Ohta, "Regiospecific Synthesis of 2-Substituted Furanonaphthoquinones," Journal of Heterocyclic Chemistry, Jul. 1, 2000, 37:731-734.
Okano, "Introduction to Modern Pharmaceuticals," 1987, revised 3rd edition: 111, translation 4 pages.
Orshal and Khalil, "Interleukin-6 Impairs Endothelium-Dependent NO-cGMP-Mediated Relaxation and Enhances Contraction in Systemic Vessels of Pregnant Rats," Am J Physiol Regul Integr Comp Physiol, 2004, 286(6):1013-1023.
Panigrahi "Gelucire: A versatile polymer for modified release drug delivery system," Future Journal of Pharmaceutical Sciences, Jun. 2018, 4(1):102-108.
Paridaens et al., "Paclitaxel Versus Doxorubicin as First-Line Single-Agent Chemotherapy for Metastatic Breast Cancer: a European Organization for Research and Treatment of Cancer Randomized Study with Cross-Over," J. Clin. Oneal. Feb. 2000; 18(4):724-33.
Patil Sharad et al., "NIR-emitting quinone-fused coumarin dyes: aqueous mediated, catalyst free sythesis and their optical properties," Tetrahedron Letters, Elsevier, Jun. 20, 2016, 57(29):3100-3104.
Pedranzini et al., "Stat3 is required for the development of skin cancer," J. Clin. Invest., 2004, 114(5):619-622.
Penning et al., "Synthesis and biological evaluation of the 1,5-diarylpyrazole class of cyclooxygenase-2 inhibitors: identification of 4-[5-(4-methylphenyl)-3-(trifluoromethyl)-1H-pyrazol-1-yl]benze nesulfonamide (SC-58635, celecoxib)," J Med Chem., Apr. 25, 1997, 40(9):1347-1365.
Perez-Sacau, et al., "Synthesis and Pharmacophore Modeling of Naphthoquinone Derivatives with Cytotoxic Activity in Human Promyelocytic Leukemia HL-60 Cell Line", J. Med. Chem., Feb. 2007, 50(4):696-706.
Peraza-Sanchez, "Cytotoxic Constituents of the Roots of Ekmanianthe Longiflora," American Chemical Society Publication—Journal of Natural Products, (2000), 63:492-495.
Pereira et al., "Invasion-Associated MMP-2 and MMP-9 are Up-Regulated Intracellularly in Concert with Apoptosis Linked to Melanoma Cell Detachment," Clinical and Experimental Metastasis, 2005, 22:285-295.
Pfitzner, et al., "The Role of STA Ts in Inflammation and Inflammatory Diseases", Curr Pharm Des, Sep. 2004, 10(23):2839-2850.

(56) References Cited

OTHER PUBLICATIONS

Pillai et al., "Effects of transient overexpression or knockdown of cytochrome P450 reductase on reactive oxygen species generation and hypoxia reoxygenation injury in liver cells," Dept of Pharma Sci., Dec. 2011, 38(12):846-853.
Pinzon-Guzman, "Protein kinase C regulates rod photoreceptor differentiation through modulation of STAT3 signalinq", Adv Exp Med Biol, 2010, 664:21-28.
Poli et al., "STAT3-mediated metabolic reprograming in cellular transformation and implications for drug resistance," Frontiers in Oncology, Jun. 8, 2015, 5(121):6 pages.
Ponti, "Isolation and In Vitro Propagation of Tumorigenic Breast Cancer Cells with Stem/Progenitor Cell Properties," Cancer Res, 2005, 65(13):5506-11.
Porter "New insights into the role of cytochrome P450 reductase (POR) in microsomal redox biology," Acta Pharmaceutical Sinica., 2012, 2(2):102-106.
Price, "Computational Methodologies: Toward Crystal Structure and Polymorph Prediction," Polymorphism in Pharmaceutical Solids, CRC Press, Boca Raton, FL, 2009, 2nd edition, 31 pages.
Prince, "Identification of a Subpopulation of Cells with Cancer Stem Cell Properties in Head and Neck Squamous Cell Carcinoma," Proc Natl Acad Sci USA, 2007, 104(3):973-978.
Punjabi et al., "Persistent activation of STAT3 by latent Kaposi's sarcoma-associated herpesvirus infection of endothelial cells", J Viral, (2007), 81(5):2449-2458.
Puthier et al., "IL-6 Up-Regulates MCL-1IN Human Myeloma Cells through JAK/STAT rather than ras/MAP Kinase Pathway," Eur J Immunol, 1999, 29(12):3945-3950.
Qui et al., "RNA interference-mediated signal transducers and activators of transcription 3 gene silencing inhibits invasion and metastasis of human pancreatic cancer cells," Cancer Sci. 2007, 98(7):1099-1106.
Qiuwen et al., "Evaluation of the Potential Cancer Chemotherapeutic Efficacy of Natural Product Isolates Employing in Vivo Hallow Fiber Tests," J. Nat. Prod. 2002, 65(6):842-850.
Rahaman et al., "Inhibition of constitutively active Stat3 suppresses proliferation and induces apoptosis in glioblastoma multiforme cells," Oncogene, 2002, 21(55):8404-8413.
Rao and Kingston, "Plant Anticancer Agents. XII. Isolation and Structure Elucidation of New Cytotoxic Quinones from Tabebuia Cassinoides," Journal of Natural Products, 1982, 45(5):600-604.
Rawat et al., "Constitutive activation of STAT3 is associated with the acquisition of an interleukin 6-independent phenotype by murine plasmacytomas and hybridomas," Blood, 2000, 96(10):3514-3521.
Reagan-Shaw, "Dose Translation from Animal to Human Studies Revisited," The FASEB Journal, 2007, 22(3):659-661.
Ricci-Vitiani, "Identification and Expansion of Human Colon-Cancer-Initiating Cells," Nature. 2007, 445(7123):111-115.
Rieber et al., "Relationship of Mcl-1 isoforms, ratio p21WAF1/cyclin A, and Junkinase phosphorylation to apoptosis in human breast carcinomas", Biochemical and Biophysical Research Communications, 2002, 297:943-949.
Rieber et al., "Mcl-1 cleavage and sustained phosphorylation of c-Jun-N-terminal kinase mediate melanoma apoptosis induced by 2-acetyl furanonaphthoquinone," Cancer Biology and Therapy, 2008, 7(8):1206-1211.
Ried et al., "State of the art: diagnostic tools and innovative therapies for treatment of advanced thymoma and thymic carcinoma," Eur J Cardiothorac Surg., Jun. 2016, 49(6):1545-1552.
Roder, "STAT3 is Constitutively Active in Some Patients with Polycythemia Rubra Vera," Exp Hematol, 2001, 29(6):694-702.
Romano et al., "The therapeutic promise of disrupting the PD-1/PD-L1 immune checkpoint in cancer: unleashing the CD8 T cell mediated anti-tumor activity results in significant, unprecedented clinical efficacy in various solid tumors," J Immunother Cancer., Apr. 21, 2015, 3:15, 5 pages.
Rosen et al., "The role of constitutively active signal transducer and activator of transcription 3 in ovarian tumorigenesis and prognosis," Cancer, 2006, 107(11):2730-2740.
Rouhi, "The Right Stuff," Chemical & Engineering News, 81(8):32-35.
Rowland et al., "Clinical Pharmacokinetics: Concepts and Applications," Lippincott Williams & Wilkins, 1995, 4th edition, Front Matter.
Ryu et al., "Synthesis and antifungal activity of furo[2,3-f]quinolin-5-ols," Bioorg Med Chem Lett., Feb. 1, 2011, 21(3):952.
Sano et al., "STAT3 Links Activated Keratinocytes and Immunocytes Required for Development of Psoriasis in a Novel Transgenic Mouse Model", Nat Med, 2005, 11(1):43-49.
Savarese et al., "Coexpression of oncostatin M and its receptors and evidence for STAT3 activation in human ovarian carcinomas," Cytokine, 2002, 17(6):324-334.
Schaefer et al., "Constitutive activation of Stat3alpha in brain tumors: localization to tumor endothelial cells and activation by the endothelial tyrosine kinase receptor (VEGFR-2)," Oncogene, 2002, 21(13):2058-2065.
Schatton, "Identification of Cells Initiating Human Melanomas," Nature. 2008, 451(7176):345-349.
Scheper, "Sulindac induces apoptosis and inhibits tumor growth in vivo in head and neck squamous cell carcinoma", Neoplasia, 2007, 9(3):192-199.
Schlette, "Survivin Expression Predicts Poorer Prognosis in Anaplastic Large-Cell Lymphoma," J Clin Oncol, 2004, 22(9):1682-1688.
Scholz et al., "Activated signal transducer and activator of transcription 3 (STAT3) supports the malignant phenotype of human pancreatic cancer", Gastroenterolgy, 2003, 125:891-905.
Schumacher et al., "Reactive Oxygen Species in Cancer: A Dance with the Devil," Cell Press Canc Cell., Feb. 9, 2015, 27(2):156-157.
Sengupta, "Activation of Monocycle Effector Genes and STAT Family Transcription Factors by Inflammatory Synovial Fluid is Independent of Interferon Gamma," J Exp Med, 1995, 181(3):1015-1025.
Shaikh et al., "Streptonigrin. 1. Structure-activity relationships among simple bicyclic analogues. Rate dependence of DNA degradation on quinone reduction potential," J Med Chem., 1986, 29(8):1329-1340.
Shen, et al., "Synthesis and antiproliferative activity of indolizinophthalazine-5,12-dione derivatives, DNA topoisomerase IB inhibitors," European Journal of Medicinal Chemistry, 2010, 45(9):3938-3942.
Shouda, "Induction of the Cytokine Signal Regulator SOCS3/CIS3 as a Therapeutic Strategy for Treating Inflammatory Arthritis," J Clin Invest, 108(12):1781-1788.
Siegel et al.,"NAD(P)H: Quinone Oxidoreductase 1 (NQO1) in the Sensitivity and Resistance to Antitumor Quinones," Biochem Pharmacol., Apr. 15, 2012, 83(8):1033-1040.
Silver et al., "Activated signal transducer and activator of transcription (STAT) 3: localization in focal adhesions and function in ovarian cancer cell motility," Cancer Res. 2004, 64(10):3550-3558.
Simamura et al., "Furanonaphthoquinones Cause Apoptosis of Cancer Cells by Inducing the Production of Reactive Oxygen Species by the Mitochondrial Voltage-Dependent Anion Channel", Cancer Biology & Therapy, Nov. 2006, 5(11):1523-1529.
Simeone-Penney, "Airway Epithelial STAT3 Is Required for Allergic Inflammation in a Murine Model of Asthma," J Immunol, 178(10):6191-6199.
Singh, "Identification of a Cancer Stem Cell in Human Brain Tumors," Cancer Res, 2003, 63(18):5821-5828.
Solorzano et al., "Decreased Glycolytic Metabolism Accelerates Apoptosis in Response to 2-Acetyl Furanonaphthoquinone in K1735 Melanoma Irrespective of BCL-2 Overexpression," Cancer Biol. Ther., Mar. 2005, 4(3):329-335.
Sommer et al., "In vivo activation of STAT3 in cutaneous T-cell lymphoma. Evidence for an antiapoptotic function of STAT3," Leukemia, 2004, 18(7):1288-1295.
Song and Grandis, "STAT Signaling in Head and Neck Cancer," Onogene, 2000, 19(21):2489-2495.
Song et al., "Activation of Stat3 by receptor tyrosine kinases and cytokines regulates survival in human non-small cell carcinoma cells," Oncogene, 2003, 22(27):4150-4165.

(56) References Cited

OTHER PUBLICATIONS

Song, "A Low-Molecular-Weight Compound Discovered Through Virtual Database Screening Inhibits Stat3 Function in Breast Cancer Cells," Proc. Natl. Acad Sci. 102(13):4700-4705.
Spiekermann et al., "Constitutive activation of STAT transcription factors in acute myelogenous leukemia," Eur J Haematol, 2001, 67(2):63-71.
Srijiwangsa et al. "Roles of NAD (P) H-Guinone Oxidoreductase 1 (NQO1) On Cancer Progression and Chemoresistance," Journal of Clinical & Experimental Oncology, 2017, 6(4):6 pages.
Steinert, "HPLC Separation and Determination of Naphtho[2,3-b]furan-4,9-Diones and Related Compounds in Extracts of Tabebuia Avellanedae (Bignoniaceae)," J Chromato, 1995, 693:281-287.
Stelmasiak, "Interleukin-6 Concentration in Serum and Cerebrospinal Fluid in Multiple Sclerosis Patients," Med Sci Monit, 2000, 6(6):1104-1108.
Stephens, "A Common Functional Variant in the Interleukin-6 gene is Associated with Increased Body Mass Index in Subjects with Type 2 Diabetes Mellitus," Mol Genet Metab, 2004, 82(2):180-186.
STN Accession No. 1985-141337 CN (141337-87-3 Registry), (May 15, 1992), 1 pg.
STN Accession No. 1986 568912.
STN Accession No. 1987-141337 CN: (141337-85-1 Registry), (May 15, 1992), 1 pg.
STN Accession No. 1989-141337 CN: (141337-89-5 Registry), (May 15, 1992), 1 pg.
STN Accession No. 1990-141337 CN: (141337-90-8 Registry),(May 15, 1992), 1 pg.
STN Accession No. 1992:245248.
STN Accession No. 1997-141337 CN: (141337-97-5 Registry), (May 15, 1992), 1 pg.
STN Accession No. 2002:33229.
STN Accession No. 2002:080446, CN: (80446-02-2 Registry), (Nov. 16, 1984), 1 oa.
STN Accession No. 33-221190,CN: (221190-33-6 Registry), (Apr. 14, 1999), 1 pg.
STN Accession No. 32-221190, CN: (221190-32-5 R, (Apr. 14, 1999), 1 pg.
STN Accession No. 31-221190, CN: (221190-31-4 REgistry), (Apr. 14, 1999),1 pg.
Stout, "No Cancer", [Online] retrieved from the internet:<http://nocancer.blogspot.com/2005/05/14-paudarco.html>, (2005).
Sun et al.,"Comparison of Effects of the Tyrosine Kinase Inhibitors AG957, AG490, and ST1571 on BCR-ASL-Expressing Cells, Demonstrating Synergy Between AG490 and ST1571," Blood, 2001, 97(7):2008-2015.
Szotek, "Ovarian Cancer Side Population Defines Cells with Stem Cell-Like Characteristics and Mullerian Inhibiting Substance Responsiveness," Proc Natl Acad Sci USA, 2006, 103(30):11154-11159.
Takano, et al., "Tumor-specific cytotoxicity and type of cell death induced by naphtho[2,3-b]furan-4,9-diones and related compounds in human tumor cell lines: relationship to electronic structure", Anticancer Research, 2009, 29:455-464.
Taylor, "Technical Data Report for Pau D'Arco," Herbal Secrets of the Rainforest, 2nd Edition, 2003.
Tefferi, "Classification, Diagnosis and Management of Myeloproliferative Disorders in the JAK2V617F era," Hamtology Am Soc Hematol Educ Program, 2006, 240-245.
Toyonaga et al., "Blockade of constitutively activated Janus kinase/signal transducer and activator of transcription-3 pathway inhibits growth of human pancreatic cancer," Cancer Lett. 2003, 201(1):107-116.
Trovato et al., "Distinctive expression of STAT3 in papillary thyroid carcinomas and a subset of follicular adenomas," Histol Histopathol., 2003, 18:393-399.
Tsareva et al., "Signal transducer and activator of transcription 3 activation promotes invasive growth of colon carcinomas through matrix metalloproteinase induction," Neoplasia, 2007, 4:279-291.
Tsutsumi et al., "Phase II Trial of Chemotherapy plus Bevacizumab as Second-Line Therapy for Patients with Metastatic Colorectal Cancer That Progressed on Bevacizumab with Chemotherapy: The Gunma Clinical Oncology Group (GCOG) trial 001 SILK Study," Oncology, Aug. 2012, 83(3):151-157.
Wang et al., "Effect of STAT3 siRNA-induced inhibition of STAT3 gene expression on the growth and apoptosis of lewis lung cancer cells", J. Clin. Oneal. 2006, 3(6):392-399.
Wang et al., "Small interfering RNA suppression of transducer and activator of transcription 3 (STAT3) signaling pathway: inhibitory effect on proliferation of human esophageal squamous carcinoma cells," Chinese Journal of Pathology, 2007, 36(6):379-383 [English Abstract].
Wang, "Identification of Cancer Stem Cell-Like Side Population Cells in Human Nasopharyngeal Carcinoma Cell Line," Cancer Res, 2007, 67(8):3716-3724.
Wang, "A Small Amphipathic a-Helical Region is Required for Transcriptional Activities and Proteasome-Dependent Turnover of the Tyrosine-Phosphorylated STATS", EMBO J, 2000, 19(3):392-399.
Wang et al., "Regulation of the Innate and Adaprive Immune Responses by STAT3 Signaling Tumor Cells", Nat Med, 2004, 10(1):48-54.
Watson & Miller, "Elevated levels of members of the STAT family of transcription factors in breast carcinoma nuclear extracts," British Journal of Cancer, 1995, 71(4):840-844.
Weber-Nordt, "Constitutive Activation of STAT Proteins in Primary Lymphoid and Myeloid Leukemia Cells and in Epstein-Barr Virus (EBV)-Related Lymphoma Cell Lines," Blood, 1996, 88(3):809-816.
Wei et al., "Stat3 activation regulates the expression of vascular endothelial growth factor and human pancreatic cancer angiogenesis and metastasis," Oncogene, 2003, 22(3):319-329.
Wermuth, "Molecular Variations Based on Isoteric Replacements," The Practice of Medicinal Chemistry, Academic Press, 1996. pp. 203-237.
Williams, "Two New Cytotoxic Naphthoquinones from Mendoncia Cowanii from the Rainforest of Madagascar," Planta Med., May 2006, 72(6):564-6.
Wyss-Coray, "Inflammation in Alzheimer disease: driving force, bystander or beneficial response?," Nat Med., Sep. 2006, 12(9):1005-1015.
Xie, et al., "Activation of stat3 in human melanoma promotes brain metastasis," Cancer Res., 2006, 66(6):3188-3196.
Xie, "STAT3 Activation Regulates the Expression of Matrix Metalloproteinase-2 and Tumor Invasion and Metastasis," Oncogene, 2004, 23(20):3550-3560.
Yafee, K, "Inflammatory Markers and Cognition in Well-Functioning African American and White Elders", Neurology, 61(1):76-80.
Yakata et al., "Expression of p-STAT3 in human gastric carcinoma: significant correlation in tumour invasion and prognosis," Int J Oncol., 2007, 30(2):437-442.
Yamashita et al., "Synthesis and evaluation of bioactive naphthoquinones from the Brazilian medical plant, *Tabebuia avellanedae*," Bioorganic & Medicinal Chemistry, 2009, 17(17):6286-6291.
Yao et al., "Experimental Study on the Growth Inhibition of Bladder Cancer Cells by Signal Conduction Blocker AG490," J. Clin. Ural., 2006, 21(5):379-382. (English Abstract).
Yardley., "nab-Paclitaxel mechanisms of action and delivery," J Control Release., Sep. 28, 2013, 170(3):365-372.
Yau et al., "Inhibition of lntegrin-Linked Kinase by QLT0254 Inhibits Akt-Dependent Pathways and is Growth Inhibitory in Orthotopic Primary Pancreatic Cancer Xenografls," Cancer Res., 2005, 65(4):1497-1504.
Yoshida et al., "Discovery and preclinical profile of teneligliptin (3-[(2S,4S)-4-[4-(3-methyl-1-phenyl-1H-pyrazol-5-yl)piperazin-1-yl]pyrrolidin-2-ylcarbonyl]thiazolidine): a highly potent, selective, long-lasting and orally active dipeptidyl peptidase IV inhibitor for the treatment of type 2 diabetes," Bioorg Med Chem., Oct. 1, 2012, 20(19):5705-5719.
Yue et al., "Synthesis and evaluation of indenopyrazoles as cyclin-dependent kinase inhibitors. 3. Structure activity relationships at C3(1,2)," J Med Chem., Nov. 21, 2002, 45(24):5233-5248.

(56) References Cited

OTHER PUBLICATIONS

Yu, H, "STAT3: Linking Oncogenesis with Tumor Immune Evasion," AACR Annual Meeting, San Diego, CA, Cancer Res (Abstract SY03-03), 68(9 Supp):1-3.
Yu, H., "The STATs of cancer—new molecular targets come of age," R., Nat Rev Cancer, 2004, 4(2):97-105.
Zani, "Furanonaphthoquinones from Tabebuia Ochracea," Phytochemistry, 1991, 30(7):2379-2381.
Zhang, "Intratumoral Delivery and Suppression of Prostate Tumor Growth by Attenuated *Salmonella enterica* serovar Typhimurium Carrying Plasmid-Based Small Interfering RNAs," Cancer Res, 2007, 67(12):5859-5864.
Zhou et al., "Activation of the PTEN/mTOR/STAT3 Pathway in Breast Cancer Stem-Like Cells is Required for Viability and Maintenance," PNAS., 104(41):16158-16163.
Zhou et al., "Corrections: Activation of the PTEN/mTOR/STAT3 Pathway in Breast Cancer Stem-Like Cells is Required for Viability and Maintenance," PNAS., 2007, 104(49):19655-19656.
Aeschi, Y, et al., "Directed Metalation Cascade To Access Highly Functionalized Thieno[2,3-f] benzofuran and Exploration as Building Blocks for Organic Electronics", Organic Letters, 15(21) particularly, compounds 5 to 8 (Scheme 2), (2013), 5586-5589.
Barret et al., "Hetero Diels-Alder Reaction with Indoloquinones", Chemical & Pharmaceutical Bulletin, 46(3), (1998), 548-550.
Buhler, Volker, Kollidon: polyvinylpyrrolidone excipients for the pharmaceutical industry, Mar. 2008, pp. 1, 2, 207-219 (Year: 2008).
Campiglia, "Unprecedented synthesis of a novel amino quinone ring system via oxidative decarboxylation of quinone-based alpha,alpha-amino esters," Organic & Biomolecular Chemistry (2010), 8(3), 622-627.
Cherkaoui et al., "Regiospecific hetero Diels-Alder synthesis of furo [2, 3-g] and furo [3, 2-g] quinoline-4, 9-diones," Tetrahedron, Jul. 8, 1996, 52(28):9499-508.
Dokduang, et al., "STATs profiling reveals predominantly-activated STAT3 in cholangiocarcinoma genesis and progression," J. Hepatobiliary Pancreat. Sci., 2014, 21:767-776.
Dorwald, Side Reactions in Organic Synthesis, 2005, Wiley: VCH, Weinheim p. IX of Preface p. 1-15.
File Registry on STN, RN 167705-94-4, entered STN: Sep. 15, 1995, 1 pg.
File Registry on STN, RN 859218-71-6, entered STN: Aug. 9, 2005, 2 pgs.
Gu et al., "Grouping solvents by statistical analysis of solvent property parameters: implication to polymorph screening," International Journal of Pharmaceutics, 2004, 283(1): 117-125.
Hayakawa, et al., "Enhanced anti-tumor effects of the PD-1/PD-L1 blockade by combining a highly absorptive form of NF-kB/STAT3 inhibitor curcumin," Journal for ImmunoTherapy of Cancer, 2014, vol. 2, Suppl.3, P210.
Hayashi, Toshimitsu, et al., "Antitumor agents. 89. Psychorubrin, a new cytotoxic naphthoquinone from Psychotria rubra and its structure-activity relationships", Journal of Medicinal Chemistry, vol. 30, No. 11, (1987), 2005-2008.
Hisahiro, Hagiwara, et al., "Domino Michael O alkylation reaction one pot synthesis of 2 4 diacylhydrofuran derivatives and its application to antitumor naphthofuran synthesis", J. Chem, Soc Perkin Trans 1, (2001), 2946-2957.
Hisahiro, Hagiwara, et al., "Tandem nucleophilic reaction leading to hydrofurans application to one pot synthesis of antitumor naphthofuran natural product", Heterocycles vol. 51 No. 3, (1999), 1 pages.
Jackson, Yvette A., et al., "Synthesis of a thiophene analogue of kuanoniamine A", A, J. Chem. Soc., Perkin Trans. particularly, compound 8 (Scheme 3), vol. 1, No. 18, (Jan. 2001), 2237-2239.
Junko, Koyama, et al., "Correlation between Cytotoxic Activities and Reduction Potentials of Heterocyclic Quinones", Molecules, vol. 15, No. 9, XP055424360, DOI: 10.3390/molecules 15096559* figure 1; table 1; compounds 4,6-8 *, (Sep. 20, 2010), 6559-6569.

Kenneth, Eyong, et al., "Semisynthesis and antitumoral activity of 2-acetylfuranonaphthoquinone and other naphthoquinone derivatives from lapachol", Bioorganic & Medicinal Chemistry Letters, (2008), 5387-5390.
Kievit, Forrest M, "Proliferation and enrichment of CD133+ glioblastoma cancer stem cells on 3D chitosanalginate scaffolds", Biomaterials, vol. 35, No. 33, (Nov. 1, 2014), 9137-9143.
Kishore "Cytotoxicity of synthesized 1,4-naphthoquinone analogues on selected human cancer cell lines" Bioorganic & Medicinal Chemistry, 2014, 22(17), 5013-5019.
Lee et al., "Facile synthesis of avicequinone-B natural product," Synthetic communications, Jan. 2002, 32(20):3099-105.
Lee, Yean Kit, "Flavopiridol disrupts STAT3/DNA interactions, attenuates STAT3-directed transcription, and combines with the Jak kinase inhibitor AG490 to achieve cytotoxic synergy", Molecular Cancer Therapeutics, 5(1), 2006, 12 pages.
Liu, Li-Jun, "Three-dimensional collagen scaffold enhances the human adenoid cystic carcinoma cancer stem cell and epithelial-mesenchymal transition properties". Journal of Biomedical Materials Research. Part B: Applied Biomaterials, vol. 102, No. 4, (May 1, 2014), 772-780.
Lu, Hong Fang, "A 3D microfibrous scaffold for long-term human pluripotent stem cell self-renewal under chemically lefined conditions", Biomaterials, Elsevier Science Publishers Bv., Barking, GB, vol. 33, No. 8, Nov. 27, 2011, 2419-2430.
Narang and Boddu, editors, Excipient Applications in Formulation Design and Drug Delivery, 2015, pp. 1-4, 299, (Year: 2015).
Ogawa, et al., "Cytotoxic Activity toward KB Cells of 2-Substituted Naptho[2,3-b]furan-4,9 diones and Their Related Compounds", Bioscience Biotechnology and Biochemistry. 70.4, (2006), 1009-1012.
Patil et al., "A Lawsone-DAMN based colorimetric chemosensor for rapid naked-eye detection of mercury (II)," New Journal of Chemistry, 2016, 40(8):6803-11.
Prasanna et al., "A facile, three-component domino protocol for the microwave-assisted synthesis of functionalized naphtho [2, 3-b] furan-4, 9-diones in water," Green chemistry, 2011, 13(8):2123-9.
Sanchez, "International Electronic Conferences on Synthetic Organic Chemistry", (2001), 1-30.
Seo, Ji-Min, et al., "JM91, a newly synthesized indoledione derivative, inhibits rat aortic vascular smooth muscle cells proliferation and cell cycle progression through inhibition of ERK1/2 and Akt activations," Biochemical Pharmacoloav 75(6), (2008), 1331-1340.
Seo, Ji-Min, et al., "YSK2821, a newly synthesized indoledione derivative, inhibits cell proliferation and cell cycle progression via the cell cycle-related proteins by regulating phosphatidylinositol-3 kinase cascade in vascular smooth muscle cells", European Journal of Pharmacology, 586(1-3), (2008), 74-81.
Shah, "The role of fluorine in medicinal chemistry Journal of Enzyme Inhibition and Medicinal Chemistry," Oct. 2007; 22(5): 527-540.
Shanab, Karem, et al., "Synthesis and antiproliferative activity of new cytotoxic azanaphthoquinone pyrrolo-annelated derivatives: Part II", Bioorganic & Medicinal Chemistry Letters vol. 21, No. 10, (2011), 3117-3121.
Simamura, et al., "Furanonaphthoquinones Cause Apoptosis of Cancer Cells by Inducing the Production of Reactive Oxygen Species by the Mitochondrial Voltage-Dependent Anion Channel", Cancer Biology & Therapy 5:11, (Nov. 2006), 1523-1529.
Simon, Karen A, "Metabolic response of lung cancer cells to radiation in a paper-based 3D cell culture system", Efiomaterials, vol. 95, (Mar. 3, 2016), 47-59.
Suh, M.E., "Comparison of QSAR Methods (CoMFA, CoMSIA, HQSAR) of Anticancer 1-N-Substituted lmidazoquinoline-4,9-dione Derivatives", Bull Korean Chem. Soc., 23(3), (2002), 417-422.
Suh, M.E., "The 3-D Qsar Study of Anticancer 1-N-substituted Imidazo- and Pyrrolo-quinoline-4,9-dione Derivatives by CoMFA and CoMSIA", Bioorganic & Medicinal Chemistry, vol. 9, No. 11, (2001), 2987-2991.
Suh, Me, et al., "Cytotoxic Effects of Pyridino [2,3-f]indole-4, 9-diones on Human Tumor Cell Lines", Biol. Pharm. Bull., 23(3), (Mar. 1, 2000), 354-355.

(56) References Cited

OTHER PUBLICATIONS

Suh, Myung_ Eun, et al., "Synthesis of lN-alkyl-2-amino-3-ethoxycarbonylpyridino[2,3-f]indole-4,9- dione derivatives (I)", STN Document No. 128:88804, 41 (5), (1997), 2 pgs.

Thieno[2,3-F]Benzofuran-6-Carboxylic Acid,4,8-Dihydro-4,8-Dioxo-2,7-Diphenyl-, Ethyl Ester (CA Index Name), Database Registry, (Aug. 9, 2005), 1 page.

Valderrama, J A, et al., "Diels-Alder Reactions of 1-Dimethylamino-1-AZA-1,3-Dienes With Benzo[b]Thiophene-4,7-Quinones", Heterocyclic Communications 9 (2), particularly, compound 11, (2003), 175-180.

Venkatesh, J. Pharm. Sci. 89, 145-54 (2000) (p. 146, left column).

Venugopalan, European Journal of Medicinal Chemistry (1989), 24(6), 611-14.

Xu, Xiao-Xi, "Encapsulated human hepatocellular carcinoma cells by alginate gel beads as an in vitro metastasis model", Experimental Cell Research, vol. 319, No. 14, (Aug. 1, 2013), 2135-2144.

Xu, Xiao-Xi, "Enrichment of cancer stem cell-like cells by culture in alginate gel beads", Journal of Biotechnology, Elsevier, Amsterdam, NL, (Mar. 4, 2014), 1-12.

Yanni, Collection of Czechoslovak Chemical Communications (1991), 56(3), 706-11.

Yanni, Journal of the Indian Chemical Society, (1990), vol. 67, pp. 777-779.

Yoon, Yeo Pyo, et al., "Preparation of indoledione derivatives for inhibiting hyper-proliferation of vascular smooth muscle cell", Accession No. 2009:161540, Document No. 150:259971, (2009), 3 pgs.

Zuloaga et al., "Regioselectivity in Diels-Alder reactions of pyranbenzoquinones," Journal of the Chemical Society, Perkin Transactions 2: Physical Organic Chemistry (1995), (5), 939-43.

NAPHTHOFURAN DERIVATIVES, PREPARATION, AND METHODS OF USE THEREOF

The present application is a 35 U.S.C. § 371 U.S. National Phase Application of PCT/US2017/063734, filed on Nov. 29, 2017, which claims the benefit of priority of U.S. Provisional Application No. 62/427,441, filed Nov. 29, 2016. The disclosures of the foregoing applications are hereby incorporated by reference in their entireties.

Cancer fatalities in the United States alone number in the hundreds of thousands each year. Despite advances in the treatment of certain forms of cancer through surgery, radiotherapy, and chemotherapy, many types of cancer are essentially incurable. Even when an effective treatment is available for a particular cancer, the side effects of such treatment can be severe and result in a significant decrease in quality of life. Most conventional chemotherapy agents have toxicity and limited efficacy, particularly for patients with advanced solid tumors. Chemotherapeutic agents cause damage to non-cancerous as well as cancerous cells. The therapeutic index of such compounds (a measure of the ability of the therapy to discriminate between cancerous and normal cells) can be quite low. Frequently, a dose of a chemotherapy drug that is effective to kill cancer cells will also kill normal cells, especially those normal cells (such as epithelial cells) which undergo frequent cell division. When normal cells are affected by the therapy, side effects such as hair loss, suppression of hematopoiesis, and nausea can occur. Depending on the general health of a patient, such side effects can preclude the administration of chemotherapy, or, at least, be extremely unpleasant and uncomfortable for the patient and severely decrease quality of the life of cancer patients. Even for cancer patients who respond to chemotherapy with tumor regression, such tumor response often is not accompanied by prolongation of progression-free survival (PFS) or prolongation of overall survival (OS). As a matter of fact, cancer often quickly progress and form more metastasis after initial response to chemotherapy. Such recurrent cancers become highly resistant or refractory to chemotherapeutics.

Recent studies have uncovered the presence of cancer stem cells (CSC, also called tumor initiating cells or cancer stem-like cells) which have self-renewal capability and are considered to be fundamentally responsible for malignant growth, relapse and metastasis. Importantly, CSCs are inherently resistant to conventional therapies. Therefore, a targeted agent with activity against cancer stem cells holds a great promise for cancer patients.

STAT3 is an oncogene which is activated in response to cytokines and/or growth factors to promote proliferation, survival, and other biological processes. STAT3 is activated by phosphorylation of a critical tyrosine residue mediated by growth factor receptor tyrosine kinases, Janus kinases, or the Src family kinases. Upon tyrosine phosphorylation, STAT3 forms homo-dimers and translocates to the nucleus, binds to specific DNA-response elements in target gene promoters, and induces gene expression. STAT3 activates genes involved in tumorigenesis, invasion, and metastasis, including Bcl-xl, Akt, c-Myc, cyclin D1, VEGF, and survivin. STAT3 is aberrantly active in a wide variety of human cancers, including all the major carcinomas as well as some hematologic tumors. Persistently active STAT3 occurs in more than half of breast and lung cancers, colorectal cancers, ovarian cancers, hepatocellular carcinomas, and multiple myelomas, etc; and more than 95% of head/neck cancers. STAT3 is considered to be one of the major mechanisms for drug resistance of cancer cells. However, STAT3 has proven a difficult target for discovering pharmaceutical inhibitor.

PCT Patent Application Publication Numbers WO2009036099, WO2009036101, WO2011116398, and WO2011116399 disclose that certain naphthofuran compounds have been shown to target cancer stem cells, inhibit non-stem cancer cells through inhibiting STAT3, and have the capability of killing many different types of cancer cells without causing damage to normal cells under certain exposure conditions. Accordingly, these naphthofuran compounds can be used for cancer treatment, especially for the treatment and prevention of refractory, recurrent, metastatic cancers, or STAT3-expressing cancers. The publications also describe certain processes for preparing naphthofuran compounds, derivatives, and intermediates thereof, and the pharmaceutical composition of relevant compounds. WO2009036099, WO2009036101, WO2011116398, and WO2011116399 are each incorporated herein by reference in their entirety.

For example, one of the naphthofuran compounds disclosed in these patent applications is one having formula (I):

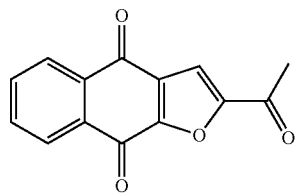

prodrugs, derivatives, pharmaceutically acceptable salts of any of the foregoing, and solvates of any of the foregoing.

Compounds having formula (I) may also be known as 2-acetylnaphtho[2,3-b]furan-4,9-dione, napabucasin, BBI-608, or BBI608, and they include tautomers thereof.

One aspect of the present disclosure relates to methods of preparing compounds having formula (I). In certain embodiments, the method comprises reacting a compound having formula (i):

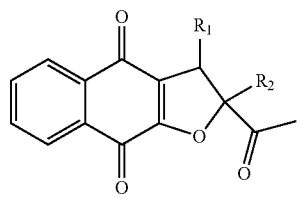

salts and solvates thereof,
with an acid;
wherein $R_1$ and $R_2$ each independently is a leaving group.

In certain embodiments, the method comprises reacting a compound chosen from dihydronaphthofuran derivatives having formula (i-a):

i-a salts and solvates thereof, with
an acid.

In certain embodiments, the method comprises reacting a compound having formula (ii):

ii salts and solvates thereof;
wherein X is O or N—$R_4$, and
$R_3$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups;
wherein $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, C(=O)$R_g$, S(=O)$_2R_e$, P(=O)$_2R_e$, C(=O)O$R_e$, C(=O)NR$_b$R$_c$, S(=O)$_2$NR$_b$R$_c$, and P(=O)$_2$NR$_b$R$_c$;
wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups,
or $R_b$ and $R_c$ together with the N to which they are bonded form a heterocycle group or a substituted heterocycle group;
$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, the method comprises reacting a compound having formula (ii-a):

ii-a salts and solvates thereof, wherein
$R_3$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, and $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, C(=O)$R_g$, S(=O)$_2R_e$, P(=O)$_2R_e$, C(=O)O$R_e$, C(=O)NR$_b$R$_c$, S(=O)$_2$NR$_b$R$_c$, and P(=O)$_2$NR$_b$R$_c$;
wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups,
or $R_b$ and $R_c$ together with the N to which they are bonded form a heterocycle group or a substituted heterocycle group;
$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and
$R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, the method comprises reacting a compound having formula (ii-b):

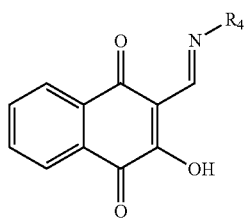

ii-b salts and solvates thereof,
  wherein $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, $C(=O)R_g$, $S(=O)_2R_e$, $P(=O)_2R_e$, $C(=O)OR_e$, $C(=O)NR_bR_c$, $S(=O)_2NR_bR_c$, and $P(=O)_2NR_bR_c$;
  wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups,
  or $R_b$ and $R_c$ together with the N to which they are bonded form a heterocycle group or a substituted heterocycle group;
  $R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and
  $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, the method comprises reacting a compound having formula (ii-c):

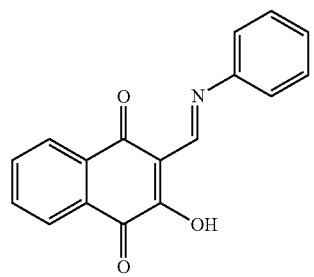

ii-c salts and solvates thereof.

In certain embodiments, the method comprises reacting a compound having formula (ii-d):

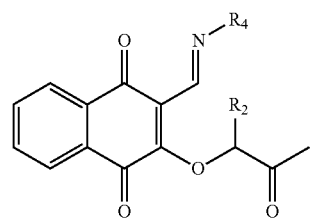

ii-d salts and solvates thereof, wherein $R_2$ is a leaving group, and
  $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, $C(=O)R_g$, $S(=O)_2R_e$, $P(=O)_2R_e$, $C(=O)OR_e$, $C(=O)NR_bR_c$, $S(=O)_2NR_bR_c$, and $P(=O)_2NR_bR_c$;
  wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups,
  or $R_b$ and $R_c$ together with the N to which they are bonded form a heterocycle group or a substituted heterocycle group;
  $R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and
  $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, the method comprises reacting a compound having formula (ii-e):

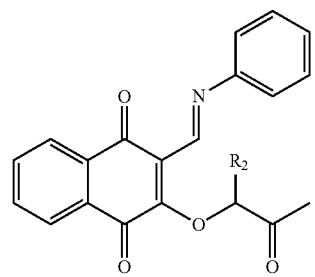

ii-e salts and solvates thereof, wherein $R_2$ is a leaving group.

In certain embodiments, the method comprises reacting a compound having formula (ii-f):

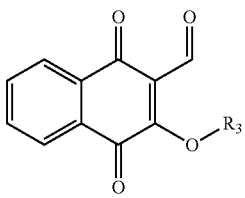

ii-f salts and solvates thereof,
wherein $R_3$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, the method comprises reacting a compound having formula (ii-g):

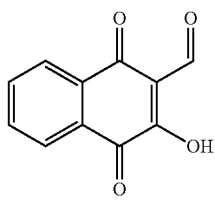

ii-g salts and solvates thereof.

In certain embodiments, the method comprises reacting a compound having formula (ii-h):

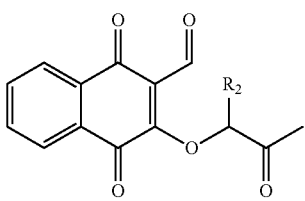

ii-h salts and solvates thereof, wherein $R_2$ is a leaving group.

In certain embodiments, the method comprises reacting a compound having formula (ii-i):

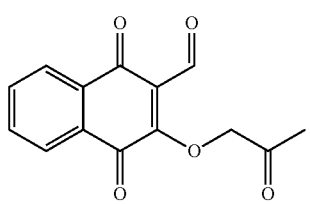

ii-i salts and solvates thereof.

In certain embodiments, the method comprises reacting a compound having formula (ii) with a compound having formula (iii):

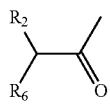

iii

In certain embodiments, the method comprises reacting a compound having formula (ii) with a compound having formula (iii-a):

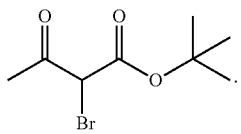

iii-a

In certain embodiments, the method comprises converting a 2-hydroxynaphthalene-1,4-dione having formula (iv):

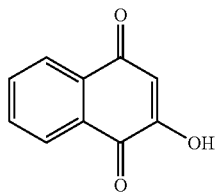

iv salts and solvates thereof,
to a compound having formula (ii).

In certain embodiments, the method comprises reacting a 2-hydroxynaphthalene-1,4-dione having formula (iv) with a compound of formula (v):

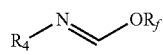

v wherein $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, $C(=O)R_g$, $S(=O)_2R_e$, $P(=O)_2R_e$, $C(=O)OR_e$, $C(=O)NR_bR_c$, $S(=O)_2NR_bR_c$, and $P(=O)_2NR_bR_c$;
wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups,
or $R_b$ and $R_c$ together with the N to which they are bonded form a heterocycle group or a substituted heterocycle group;
$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_f$ and $R_g$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, or substituted aryl groups.

Another aspect of the present disclosure relates to certain compounds that can be used to prepare compounds having formula (I). In certain embodiments, provided herein is a compound having formula (i):

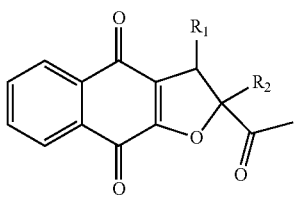

i salts and solvates thereof;
wherein $R_1$ and $R_2$ each independently is a leaving group.

In certain embodiments, provided herein is a compound having formula (i-a):

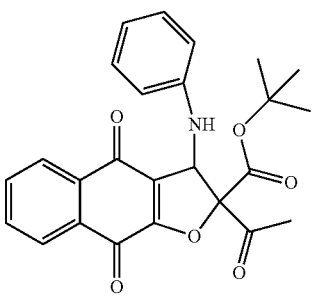

i-a salts and solvates thereof.

In certain embodiments, provided herein is a compound having formula (ii):

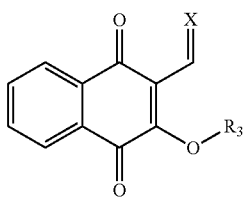

ii salts and solvates thereof;
wherein X is O or N—$R_4$, and
$R_3$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups;
wherein $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, C(=O) $R_g$, S(=O)$_2R_e$, P(=O)$_2R_e$, C(=O)O$R_e$, C(=O) N$R_bR_c$, S(=O)$_2$N$R_bR_c$, and P(=O)$_2$N$R_bR_c$;
wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups,
or $R_b$ and $R_c$ together with the N to which they are bonded form a heterocycle group or a substituted heterocycle group;
$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and
$R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, provided herein is a compound having formula (ii-a):

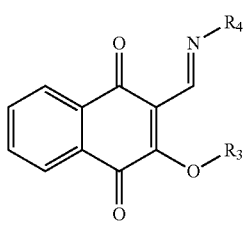

ii-a salts and solvates thereof,
wherein $R_3$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, and $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, C(=O)$R_g$, S(=O)$_2R_e$, P(=O)$_2R_e$, C(=O)O$R_e$, C(=O)N$R_bR_c$, S(=O)$_2$N$R_bR_c$, and P(=O)$_2$N$R_bR_c$;
wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, provided herein is a compound formula (ii-b):

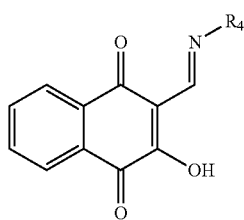

ii-b salts and solvates thereof, wherein $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, C(=O)$R_g$, S(=O)$_2R_e$, P(=O)$_2R_e$, C(=O)O$R_e$, C(=O)NR$_b$R$_c$, S(=O)$_2$NR$_b$R$_c$, and P(=O)$_2$NR$_b$R$_c$;

wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, provided herein is a compound having formula (ii-c):

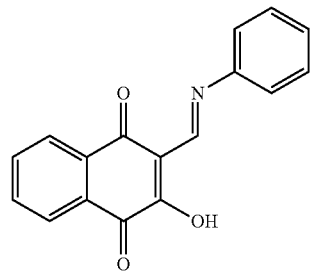

ii-c salts and solvates thereof.

In certain embodiments, provided herein is a compound having formula (ii-d):

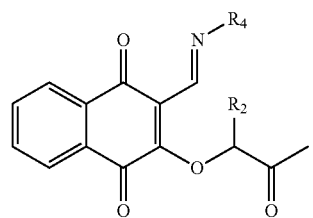

ii-d salts and solvates thereof, wherein $R_2$ is a leaving group, and $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, C(=O)$R_g$, S(=O)$_2R_e$, P(=O)$_2R_e$, C(=O)O$R_e$, C(=O)NR$_b$R$_c$, S(=O)$_2$NR$_b$R$_c$, or P(=O)$_2$NR$_b$R$_c$;

wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, provided herein is a compound having formula (ii-e):

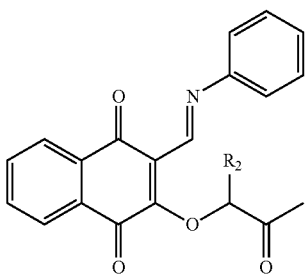

ii-e salts and solvates thereof, wherein R₂ is a leaving group.

In certain embodiments, provided herein is a compound having formula (ii-f):

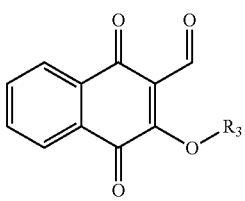

ii-f salts and solvates thereof,
wherein R₃ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, provided herein is a compound having formula (ii-g):

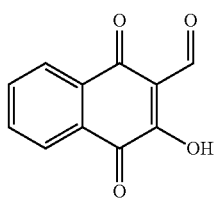

ii-g salts and solvates thereof.

In certain embodiments, provided herein is a compound having formula (ii-h):

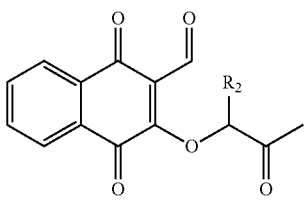

ii-h salts and solvates thereof, wherein R₂ is a leaving group.

In certain embodiments, provided herein is a compound having formula (ii-i):

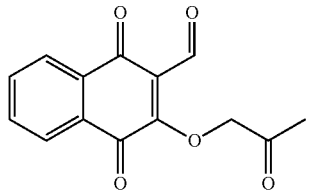

ii-i salts and solvates thereof.

Features and advantages of the present disclosure may be more readily understood by those of ordinary skill in the art upon reading the following detailed description. It is to be appreciated that certain features of the present disclosure that are, for clarity reasons, described above and below in the context of separate embodiments, may also be combined to form a single embodiment and that some features of the present disclosure that are, for brevity reasons, described in the context of a single embodiment, may also be combined so as to form sub-combinations thereof. Embodiments identified herein as exemplary are intended to be illustrative and not limiting.

Unless specifically stated otherwise, references made in the singular may also include the plural. For example, "a" and "an" may refer to either one, or one or more.

When a range of values is listed herein, it is intended to encompass each value and sub-range within that range. For example, "$C_{1-6}$ alkyl" is intended to encompass $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl. Similarly, "1-5 mg" is intended to encompass 1 mg, 2 mg, 3 mg, 4 mg, 5 mg, 1-2 mg, 1-3 mg, 1-4 mg, 1-5 mg, 2-3 mg, 2-4 mg, 2-5 mg, 3-4 mg, 3-5 mg, and 4-5 mg.

When the term "about" is used in conjunction with a numerical range, it modifies that range by extending the boundaries above and below those numerical values. In general, the term "about" is used herein to modify a numerical value above and below the stated value by a variance of 20%, 10%, 5%, or 1%. In certain embodiments, the term "about" is used to modify a numerical value above and below the stated value by a variance of 10%. In certain embodiments, the term "about" is used to modify a numerical value above and below the stated value by a variance of 5%. In certain embodiments, the term "about" is used to modify a numerical value above and below the stated value by a variance of 1%.

Definitions of specific functional groups and chemical terms are described in more detail below. General principles of organic chemistry, as well as specific functional moieties and reactivity, are described in "Organic Chemistry", Thomas Sorrell, University Science Books, Sausalito: 2006.

As used herein, the term "$C_x$-$C_y$" refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. "$C_1$-$C_{20}$" and the likes similarly encompass the some combinations between 1 and 20 (inclusive) carbon atoms, such as $C_1$-$C_6$, $C_1$-$C_{12}$, and $C_3$-$C_{12}$.

As used herein, the term "alkyl" group refers to a straight or branched chain alkane (hydrocarbon) radical. For example, the term "alkyl" group can include a $C_1$-$C_{20}$ alkyl, a $C_1$-$C_{12}$ alkyl, or a $C_1$-$C_6$ alkyl. Non-limiting examples of "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, and dodecyl. "Substituted alkyl" group refers to an alkyl group substituted with one or more substituents, such as 1 to 4 substituents, at any available point of attachment. Non-limiting examples of substituents include halogen, cyano, nitro, $CF_3$, $OCF_3$, cycloalkyl groups, alkenyl groups, cycloalkenyl groups, alkynyl groups, heterocycle groups, aryl groups, $OR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_cC(=O)$ $OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, and $NR_bP(=O)_2R_e$, wherein $R_a$ is chosen from hydrogen, alkyl groups, cycloalkyl groups, alkenyl groups, cycloalkenyl groups, alkynyl groups, heterocycle groups, and aryl groups; $R_b$, $R_c$, and $R_d$ are independently chosen from hydrogen, alkyl groups, cycloalkyl groups, heterocycle groups, and aryl groups, or $R_b$ and $R_c$ together with the N to which they are bonded form an optionally substituted heterocycle group; and $R_e$ is chosen from alkyl groups, cycloalkyl groups, alkenyl groups, cycloalkenyl groups, alkynyl groups, heterocycle groups, and aryl groups. In the aforementioned exemplary substituents, groups such as alkyl, cycloalkyl, alkenyl, alkynyl, cycloalkenyl, heterocycle, and aryl are themselves optionally substituted.

As used herein, the term "alkenyl" group refers to a straight or branched chain hydrocarbon radical having at least one carbon-carbon double bond. For example, the term "alkenyl" group can include a $C_2$-$C_{20}$ alkenyl, a $C_2$-$C_{12}$ alkenyl, or a $C_2$-$C_6$ alkenyl. Non-limiting examples of such groups include ethenyl or allyl. "Substituted alkenyl" group refers to an alkenyl group substituted with one or more substituents, such as 1 to 4 substituents, at any available point of attachment. Non-limiting examples of substituents include alkyl groups, substituted alkyl groups, as well as those groups recited above as exemplary alkyl substituents. The exemplary substituents are themselves optionally substituted.

As used herein, the term "alkynyl" group refers to a straight or branched chain hydrocarbon radical having at least one carbon-carbon triple bond. For example, the term "alkynyl" group can include a $C_2$-$C_{20}$ alkynyl, a $C_2$-$C_{12}$ alkynyl, or a $C_2$-$C_6$ alkynyl. A non-limiting example of such groups is ethynyl. "Substituted alkynyl" group refers to an alkynyl group substituted with one or more substituents, such as 1 to 4 substituents, at any available point of attachment. Non-limiting examples of substituents include alkyl groups, substituted alkyl groups, as well as those groups recited above as exemplary alkyl substituents. The exemplary substituents are themselves optionally substituted.

As used herein, the term "aryl" group refers to cyclic, aromatic hydrocarbon groups that have 1 to 5 aromatic rings, such as monocyclic or bicyclic aromatic rings such as phenyl, biphenyl, or naphthyl. Where an aryl group contains two or more aromatic rings, those aromatic rings may be joined at a single point (e.g., biphenyl) or may be fused (e.g., naphthyl, phenanthrenyl and the like). "Substituted aryl" group refers to an aryl group substituted by one or more substituents, such as 1 to 3 substituents, at any point of attachment. Non-limiting examples of substituents include nitro, cycloalkyl groups, cycloalkenyl groups, cyano, alkyl, as well as those groups recited above as exemplary alkyl substituents. The exemplary substituents are themselves optionally substituted. Non-limiting examples of substituents also include fused cyclic groups, for example fused cycloalkyl groups, fused cycloalkenyl groups, fused heterocycle groups, and fused aryl groups, where the aforementioned cycloalkyl, cycloalkenyl, heterocycle, and aryl group substituents are themselves optionally substituted.

As used herein, the term "cycloalkyl" group refers to a fully saturated cyclic hydrocarbon group having 1 to 4 rings and 3 to 8 carbons per ring. Non-limiting examples of such groups include cyclopropyl, cyclobutyl, cyclopentyl, cyclohexyl, and cycloheptyl. "Substituted cycloalkyl" group refers to a cycloalkyl group substituted with one or more substituents, such as 1 to 4 substituents, at any available point of attachment. Non-limiting examples of substituents include nitro, cyano, alkyl, substituted alkyl, as well as those groups recited above as exemplary alkyl substituents. The exemplary substituents are themselves optionally substituted. Non-limiting examples of substituents also include spiro-attached or fused cyclic substituents, such as spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents are themselves optionally substituted.

As used herein, the term "cycloalkenyl" group refers to a partially unsaturated cyclic hydrocarbon group containing 1 to 4 rings and 3 to 8 carbons per ring. Non-limiting examples of such groups include cyclobutenyl, cyclopentenyl, and cyclohexenyl. "Substituted cycloalkenyl" refers to a cycloalkenyl group substituted with one more substituents, such as 1 to 4 substituents, at any available point of attachment. Non-limiting examples of substituents include nitro, cyano, alkyl groups, as well as those groups recited above as exemplary alkyl substituents. The exemplary substituents are themselves optionally substituted. Non-limiting examples of substituents also include spiro-attached or fused cyclic substituents, such as spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents are themselves optionally substituted.

The term "carbocyclic" group refers to aromatic or non-aromatic 3 to 7 membered monocyclic, 7 to 11 membered bicyclic, and 8 to 16 membered tricyclic groups, in which all atoms of the ring or rings are carbon atoms. "Substituted carbocyclic" group refers to a carbocyclic group substituted with one or more substituents, such as 1 to 4 substituents, at any available point of attachment. Non-limiting examples of substituents include nitro, cyano, $OR_a$, wherein $R_a$ is as defined hereinabove, as well as those groups recited above as exemplary cycloalkyl substituents. The exemplary substituents are themselves optionally substituted.

As used herein, the terms "heterocycle" and "heterocyclic" groups refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) that have at least one heteroatom in at least one carbon atom-containing ring. Each ring of the heterocyclic group containing a heteroatom may have 1, 2, 3, or 4 heteroatoms selected from nitrogen atoms, oxygen atoms, and/or sulfur atoms, where the nitrogen and sulfur heteroatoms are optionally oxidized and the nitrogen heteroatoms are optionally quaternized. The term "heteroarylium" refers to a heteroaryl group bearing a quaternary nitrogen atom and thus a positive charge. The heterocyclic group may be attached to the remainder of the molecule at any heteroatom or carbon atom of the ring or ring system. Non-limiting examples of monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, triazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), triazinylazepinyl, and tetrahydroquinolinyl. Non-limiting examples of tricyclic heterocyclic groups include carbazolyl, benzidolyl, phenanthrolinyl, acridinyl, phenanthridinyl, and xanthenyl.

As used herein, "substituted heterocycle" and "substituted heterocyclic" (such as "substituted heteroaryl") groups refer to heterocycle or heterocyclic groups substituted with one or more substituents, such as 1 to 4 substituents, at any available point of attachment. Non-limiting examples of substituents include cycloalkyl groups, cycloalkenyl groups, nitro, oxo (i.e., =O), cyano, alkyl, as well as those groups recited above as exemplary alkyl substituents. The exemplary substituents are themselves optionally substituted. Non-limiting examples of substituents also include spiro-attached or fused cyclic substituents at any available point or points of attachment, such as spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle and aryl substituents are themselves optionally substituted.

As used herein, the term "halogen" includes fluorine (F), chlorine (Cl), bromine (Br), and iodine (I).

It will be appreciated that the compounds, as described herein, may be substituted with any number of substituents or functional moieties. Throughout the disclosure, groups and substituents thereof may be chosen to provide stable moieties and compounds. Unless otherwise indicated, any heteroatom with unsatisfied valences is assumed to have hydrogen atoms sufficient to satisfy the valences.

Certain compounds of the present disclosure may exist in particular geometric or stereoisomeric forms. The present disclosure contemplates all such compounds, including cis and trans-isomers, R- and S-enantiomers, diastereomers, (D)-isomers, (L)-isomers, the racemic mixtures thereof, and other mixtures thereof, as falling within the scope of the present disclosure. Additional asymmetric carbon atoms may be present in a substituent such as an alkyl group. All such isomers, as well as mixtures thereof, are intended to be included in the present disclosure.

Isomeric mixtures containing any of a variety of isomer ratios may be utilized in accordance with the present disclosure. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present disclosure. Those of ordinary skill in the art will readily appreciate that analogous ratios are contemplated for more complex isomer mixtures.

If, for instance, a particular enantiomer of a compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

One of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In certain embodiments, a protecting group reacts selectively in good yield to give a protected substrate that is stable to the projected reactions; the protecting group should be selectively removable in good yield by non-toxic reagents that do not attack the other functional groups and that may be readily available; the protecting group forms an easily separable derivative (in certain embodiments, without the generation of new stereogenic centers); and the protecting group has a minimum of additional functionality to avoid further sites of reaction. Oxygen, sulfur, nitrogen, and carbon protecting groups may be utilized. Non-limiting examples of protecting groups can be found in Protective Groups in Organic Synthesis, Third Ed. Greene, T. W. and Wuts, P. G., Eds., John Wiley & Sons, New York: 1999.

As used herein, the term "leaving group" refers to a group that can be substituted by another group in a substitution reaction or that can be removed in an elimination reaction (e.g., an electronic cascade reaction or a spirocyclization reaction). Within either of these categorical definitions exemplary leaving groups include, but are not limited to, H, an halide (fluoride, chloride, bromide, and iodide), an azide, a sulfonate (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), succinimide-N-oxide, p-nitrophenoxide, pentafluorophenoxide, tetrafluorophenoxide, $OR_a$, $NR_bR_c$, a carboxylate, an aminocarboxylate (carbamate), and an alkoxycarboxylate (carbonate); where $R_a$ is chosen from hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, alkynyl groups, substituted alkynyl groups, heterocycle groups, substituted heterocycle groups, aryl groups, and substituted aryl groups; and $R_b$ and $R_c$ each is independently chosen from hydrogen, alkyl groups, substituted alkyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group. In certain embodiments satisfying one definition given above, the leaving group is H. In other certain embodiments, the leaving group is chosen from halides (fluoride, chloride, bromide, and iodide). In certain embodiments, the leaving group is chosen from sulfonates (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate). In certain embodiments, the leaving group is chosen from succinimide-N-oxide, p-nitrophenoxide, and pentafluorophenoxide, tetrafluorophenoxide. In certain embodiments, the leaving group is an azide. In certain embodiments, the leaving group is chosen from aminocarboxylates (carbamates). In certain embodiments, the leaving group is chosen from carboxylates (e.g., —COOH or —COO⁻), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, the leaving group is chosen from $OR_a$ and $NR_bR_c$, where $R_a$ is chosen from hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, alkynyl groups, substituted alkynyl groups, heterocycle groups, substituted heterocycle groups, aryl groups, and substituted aryl groups; and $R_b$ and $R_c$ each is independently chosen from hydrogen, alkyl groups, substituted alkyl groups, cycloalkyl groups, substituted cycloalkyl groups, heterocycle groups, substituted heterocycle groups, aryl groups, or substituted aryl groups, or $R_b$ and $R_c$ together with the N to which they are bonded form a heterocycle group or a substituted heterocycle group.

Compounds of the present disclosure may, subsequent to their preparation, be isolated and/or purified to obtain a composition containing an amount by weight equal to or greater than 90% ("substantially pure"), which may then be used and/or formulated as described herein. In certain embodiments, the compounds of the present disclosure are more than 95% pure. In certain embodiments, the compounds of the present disclosure are more than 99% pure.

As used herein, a solid form of the present disclosure is "substantially pure" when it accounts for an amount by weight equal to or greater than 90% of the sum of all solid form(s) in a sample as determined by a method in accordance with the art, such as quantitative XRPD. In certain embodiments, the solid form is "substantially pure" when it accounts for an amount by weight equal to or greater than 95% of the sum of all solid form(s) in a sample. In certain embodiments, the solid form is "substantially pure" when it accounts for an amount by weight equal to or greater than 99% of the sum of all solid form(s) in a sample.

Solvates of the compounds of the present disclosure are also contemplated herein. The term "solvate" refers to an aggregate that comprises one or more molecules of a compound of the present disclosure and one or more molecules of a solvent or solvents, such as in fixed stoichiometric ratios. Solvates of the compounds of the present disclosure include, for example, hydrates.

As used herein, the term "solid form" or "Form" refers to a crystal form and/or amorphous form of a solid material.

As used herein, the terms "crystal form" and "crystalline form" can be used interchangeably to denote polymorphs and pseudo-polymorphs of a crystalline solid.

As used herein, the term "polymorph" refers to a crystal structure in which a compound can crystallize. Different polymorphs have different molecular packing arrangements in the crystal lattice but all share the same chemical composition.

Crystal forms can be identified and distinguished from each other by one or more analytical tests and/or physical properties such as, for example, X-ray powder diffraction (XRPD), single crystal X-ray diffraction, differential scanning calorimetry (DSC), dynamic vapor sorption (DVS), and/or thermogravimetric analysis (TGA).

As used herein, the term "polymorphism" denotes the ability of a compound to form more than one polymorph.

As used herein, the terms "solvate" and "pseudo-polymorph" can be used interchangeably to denote a crystal having either stoichiometric or nonstoichiometric amounts of a solvent incorporated in the crystal lattice. If the incorporated solvent is water, the solvate formed is a "hydrate". When the incorporated solvent is alcohol, the solvate formed is an "alcoholate".

As used herein, a "metastable" form is a crystal form which does not have the highest rank order of thermodynamic stability.

As used herein, the term "amorphous form" denotes a solid material which does not possess a distinguishable crystal lattice and the molecular arrangement of molecules lacks a long-range order. In particular, amorphous denotes a material that does not show any sharp Bragg diffraction peak.

As used herein, the term "X-ray powder diffraction pattern" or "XRPD pattern" refers to an experimentally obtained diffractogram. X-ray powder diffraction patterns plot peak positions (abscissa) versus peak intensities (ordinate).

As used herein, the term "XRPD" refer to the analytical method of X-Ray Powder Diffraction. XRPD patterns can be recorded at ambient conditions in transmission geometry with a diffractometer. For an amorphous material, an XRPD pattern may include one or more broad peaks; and for a crystalline material, an XRPD pattern may include one or more peaks, each identified by its angular value as measured in degrees 2θ. The repeatability of the angular values is in the range of ±0.2° 2θ, i.e., the angular value can be the angular value +0.2°, the angular value −0.2°, or any value between those two end points (angular value +0.2° and angular value −0.2°).

As used herein, the term "DSC" refers to the analytical method of Differential Scanning calorimetry.

As used herein, the term "onset" refers to the intersection point of the baseline before transition and the interflection tangent.

As used herein, the term "glass transition temp" (Tg) refers to the temperature above which a glassy amorphous solid becomes rubbery.

As used herein, the term "TGA" refers to the analytical method of Thermo Gravimetric Analysis.

As used herein, the term "solvent" refers to any liquid in which the product is at least partially soluble (e.g., solubility of product >1 g/l).

As used herein, the term "acceptable" refers to being compatible with the other ingredients of the formulation and not injurious to the patient.

As used herein, the term "prodrug" refers to a pharmacological derivative of a parent drug molecule that requires biotransformation, either spontaneous or enzymatic, within the organism to release the active drug. Such prodrugs then are pharmaceutically active in vivo, when they undergo solvolysis under physiological conditions or undergo enzymatic degradation. Prodrug compounds herein may be called single, double, triple, etc., depending on the number of biotransformation steps required to release the active drug within the organism, and the number of functionalities present in a precursor-type form.

Prodrug forms often offer advantages of solubility, tissue compatibility, or delayed release in the mammalian organism. Prodrugs commonly known in the art include well-known acid derivatives, such as, for example, esters prepared by reaction of the parent acids with a suitable alcohol, amides prepared by reaction of the parent acid compound with an amine, basic groups reacted to form an acylated base derivative, etc. Other prodrug derivatives may be combined with other features disclosed herein to enhance bioavailability. Accordingly, those of skill in the art will appreciate that certain of the presently disclosed compounds having free amino, amido, hydroxy or carboxylic groups can be converted into prodrugs. Prodrugs include compounds having an amino acid residue, or a polypeptide chain of two or more (e.g., two, three, or four) amino acid residues which are covalently joined through peptide bonds to free amino, hydroxy or carboxylic acid groups of the presently disclosed compounds. The amino acid residues include the 20 naturally occurring amino acids commonly designated by three letter symbols and also include 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Prodrugs also include compounds having a carbonate, carbamate, amide and/or alkyl ester moiety covalently bonded to any of the above substituents disclosed herein.

One aspect of the present disclosure relates to methods of making compounds having formula (I). In certain embodiments, the method comprises reacting a compound having formula (i)

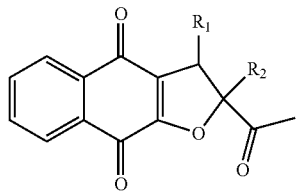

i salts and solvates thereof, with an acid; wherein $R_1$ and $R_2$ each independently is a leaving group.

In certain embodiments, the method comprises reacting a compound of formula (i) with an acid. In certain embodiments, the acid comprises an inorganic acid or an organic acid. In certain embodiments, the acid comprises an inorganic acid. In certain embodiments, the acid comprises an acid chosen from sulfuric acid ($H_2SO_4$), phosphoric acid ($H_3PO_4$), nitric acid ($HNO_3$), perchloric acid ($HClO_4$), hydrofluoric acid (HF), hydrochloric acid (HCl), hydrobromic acid (HBr), or hydroiodic acid (HI). In certain embodiments, the acid comprises an acid chosen from sulfuric acid ($H_2SO_4$), phosphoric acid ($H_3PO_4$), or hydrochloric acid (HCl). In certain embodiments, the acid comprises sulfuric acid ($H_2SO_4$). In certain embodiments, the acid comprises phosphoric acid ($H_3PO_4$). In certain embodiments, the acid comprises hydrochloric acid (HCl).

In certain embodiments, the acid comprises an organic acid. In certain embodiments, the acid comprises an acid chosen from carboxylic acids and sulfonic acids, where each of the carboxylic acids and sulfonic acids optionally is substituted. In certain embodiments, the acid comprises an acid chosen from carboxylic acids, halocarboxylic acids, or anhydrides thereof. In certain embodiments, the acid comprises an acid chosen from formic acid, acetic acid, acetic anhydride, propionic acid, propionic anhydride, fluoroacetic acid, trifluoroacetic acid, trifluoroacetic anhydride, chloroacetic acid, chloroacetic anhydride, dichloracetic acid, trichloroacetic acid, citric acid, gluconic acid, lactic acid, oxalic acid, tartaric acid, methanesulfonic acid, ethanesulfonic acid, benzenesulfonic acid, toluenesulfonic acid, trifluoromethanesulfonic acid, naphthalenesulfonic acid, polystyrenesulfonic acid, and ascorbic acid. In certain embodiments, the acid comprises an acid chosen from formic acid, acetic acid, acetic anhydride, trifluoroacetic acid, trifluoroacetic anhydride, chloroacetic acid, chloroacetic anhydride, methanesulfonic acid, benzenesulfonic acid, and toluenesulfonic acid. In certain embodiments, the acid comprises formic acid. In certain embodiments, the acid comprises acetic acid. In certain embodiments, the acid comprises acetic anhydride. In certain embodiments, the acid comprises trifluoroacetic acid. In certain embodiments, the acid comprises methanesulfonic acid.

In certain embodiments, the acid comprises an inorganic acid and an organic acid. In certain embodiments, the ratio of the inorganic acid to the organic acid is from about 0.1 to about 20, about 0.2 to about 10, about 0.5 to about 5, about 0.5, about 0.6, about 0.7, about 0.8, about 0.9, about 1, about 1.2, about 1.5, or about 2.

In certain embodiments, the method comprises reacting a solution of the compound (i) with an acid. In certain embodiments, the solution of compound (i) comprises a solvent chosen from protic solvents or aprotic solvents. In certain embodiments, the solution comprises a solvent chosen from water-miscible solvents and water-immiscible solvents. In certain embodiments, the solution comprises a solvent chosen from organic acids, alcohols, esters, amines, amides, aminoalcohols, ethers, sulfoxides, and heteroaromatics. In certain embodiments, the solution comprises a solvent chosen from acetone, acetonitrile, ethyl acetate, isopropyl acetate, dimethylformamide (DMF), N-methylpyrrolidone (NMP), dimethylimidazolidinone (DMI), dimethylsulfoxide (DMSO), dioxane, methanol, ethanol, propanol, iso-propanol, formic acid, acetic acid, propanoic acid, pyridine, and tetrahydrofuran. In certain embodiments, the solution comprises a solvent chosen from isopropyl acetate, dimethylformamide (DMF), N-methylpyrrolidone (NMP), or dimethylimidazolidinone (DMI). In certain embodiments, the solution comprises isopropyl acetate. In certain embodiments, the solution comprises dimethylformamide (DMF). In certain embodiments, the solution comprises N-methylpyrrolidone (NMP). In certain embodiments, the solution comprises dimethylimidazolidinone (DMI).

In certain embodiments, the ratio of the acid to the solution of the compound (i) is from about 0.1 to about 50, about 0.5 to about 20, about 1 to about 10, about 1 to about 5, about 1, about 2, about 3, or about 4.

In certain embodiments, the method comprises reacting the compound (i) with a base. In certain embodiments, the base comprises an inorganic base or an organic base. In certain embodiments, the base comprises a base chosen from LiOH, NaOH, KOH, $Na_2CO_3$, $NaHCO_3$, and ammonia.

In certain embodiments, the reaction comprises dissolving compound (i) in dimethylformamide (DMF). In certain embodiments, the reaction comprises adding the DMF solution into an acid mixture comprising sulfuric acid and acetic acid. In certain embodiments, the concentration of sulfuric acid in the acid mixture is from about 10% to about 90%, about 20% to about 80%, about 20%, about 30%, about 40%, about 50%, about 60%, or about 70%. In certain embodiments, the reaction temperature is from about 0° C. to about 80° C. In certain embodiments, the reaction temperature is about 10° C., about 15° C., about 20° C., about 25° C., about 30° C., about 35° C., about 40° C., or about 50° C. In certain embodiments, the reaction comprises mixing the reaction mixture with water.

In certain embodiments, $R_1$ is chosen from halides, $OR_a$, and $NR_bR_c$; where $R_a$ is chosen from hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, alkynyl groups, substituted alkynyl groups, heterocycle groups, substituted heterocycle groups, aryl groups, and substituted aryl groups; and $R_b$ and $R_c$ each is independently chosen from hydrogen, alkyl groups, substituted alkyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group. In certain embodiments, $R_1$ is chosen from Cl, Br, I, $OR_a$, and $NR_bR_c$; where $R_a$ is chosen from hydrogen, alkyl groups, substituted alkyl groups, cycloalkyl groups, substituted cycloalkyl groups, heterocycle groups, substituted heterocycle groups, aryl groups, and substituted aryl groups; and $R_b$ and $R_c$ each is independently chosen from hydrogen, alkyl groups, substituted alkyl groups, cycloalkyl groups, substituted cycloalkyl groups, heterocycle groups, substituted heterocycle groups, aryl groups, and substituted aryl groups. In certain embodiments, $R_1$ is chosen from Cl, Br, I, and $NR_bH$; where $R_b$ is chosen from alkyl groups, substituted alkyl groups, cycloalkyl groups, substituted cycloalkyl groups, aryl groups, and substituted aryl groups. In certain embodiments, $R_1$ is $NR_bH$, where $R_b$ is phenyl or substituted phenyl.

In certain embodiments, $R_2$ is chosen from H, halides, sulfonates (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), an azide, carboxylates (e.g., —COOH or —COO—), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, $R_2$ is chosen from H, halides, carboxylates (e.g., —COOH or —COO—), alkoxycarboxylates (e.g., methoxycarboxylate, ethoxycarboxylate, isopropoxycarboxylate, or tert-butoxycarboxylate), or aroxycarboxylates (e.g., phenoxycarboxylate, methylphenoxycarboxylate). In certain embodiments, $R_2$ is chosen from H, Cl, Br, I, —COOH, —COO—, methoxycarboxylate, ethoxycarboxylate, isopropoxycarboxylate, tert-butoxycarboxylate, phenoxycarboxylate, and methylphenoxycarboxylate. In certain embodiments, $R_2$ is chosen from H, Cl, Br, —COOH, —COO$^-$, methoxycarboxylate, ethoxycarboxylate, isopropoxycarboxylate, and tert-butoxycarboxylate. In certain embodiments, $R_2$ is H. In certain embodiments, $R_2$ is tert-butoxycarboxylate.

In certain embodiments, the method comprises reacting a compound having formula (i-a):

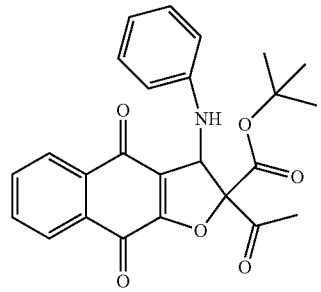

i-a salts and solvates thereof, with an acid.

In certain embodiments, the method comprises reacting a compound having formula (ii):

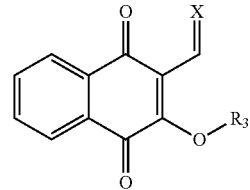

ii salts and solvates thereof;

wherein $R_3$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, and X is O or N—$R_4$;

wherein $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, C(=O)$R_g$, S(=O)$_2R_e$, P(=O)$_2R_e$, C(=O)O$R_e$, C(=O)N$R_bR_c$, S(=O)$_2$N$R_bR_c$, and P(=O)$_2$N$R_bR_c$;

wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, X is N—$R_4$. In certain embodiments, the method comprises reacting a compound having formula (ii-a):

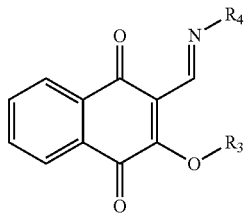

ii-a salts and solvates thereof, wherein $R_3$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, and $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, $C(=O)R_g$, $S(=O)_2R_e$, $P(=O)_2R_e$, $C(=O)OR_e$, $C(=O)NR_bR_c$, $S(=O)_2NR_bR_c$, and $P(=O)_2NR_bR_c$;

wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, $R_3$ is hydrogen. In certain embodiments, the method comprises reacting a compound having formula (ii-b):

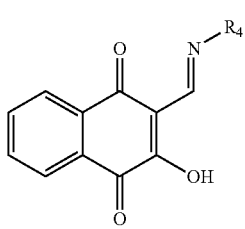

ii-b salts and solvates thereof, wherein $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, $C(=O)R_g$, $S(=O)_2R_e$, $P(=O)_2R_e$, $C(=O)OR_e$, $C(=O)NR_bR_c$, $S(=O)_2NR_bR_c$, and $P(=O)_2NR_bR_c$;

wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, $R_4$ is chosen from alkyl groups, substituted alkyl groups, cycloalkyl groups, substituted cycloalkyl groups, heterocycle groups, substituted heterocycle groups, aryl groups, and substituted aryl groups. In certain embodiments, $R_4$ is chosen from alkyl groups, cycloalkyl groups, heterocycle groups, and aryl groups. In certain embodiments, $R_4$ is chosen from methyl, ethyl, isopropyl, tert-butyl, cyclopentyl, cyclohexyl, cycloheptyl, phenyl, pyridyl, and pyrrolyl. In certain embodiments, $R_4$ is chosen from phenyl, pyridyl, and pyrrolyl. In certain embodiments, $R_4$ is phenyl.

In certain embodiments, $R_4$ is chosen from $C(=O)R_g$, $S(=O)_2R_e$, $P(=O)_2R_e$, $C(=O)OR_e$, $C(=O)NR_bR_c$, $S(=O)_2NR_bR_c$, and $P(=O)_2NR_bR_c$; wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group; $R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups. In certain embodiments, $R_4$ is $C(=O)R_g$, wherein $R_g$ is chosen from alkyl groups, substituted alkyl groups, cycloalkyl groups, substituted cycloalkyl groups, aryl groups, and substituted aryl groups. In certain embodiments, $R_4$ is $C(=O)R_g$, wherein $R_g$ is chosen from methyl, ethyl, propyl, isopropyl, butyl, t-butyl, phenyl, and substituted phenyl. In certain embodiments, $R_4$ is $C(=O)OR_e$, wherein $R_e$ is chosen from methyl, ethyl, propyl, isopropyl, butyl, t-butyl, phenyl, and substituted phenyl. In certain embodiments, $R_4$ is $S(=O)_2R_e$, wherein $R_e$ is chosen from alkyl groups, substituted alkyl groups, cycloalkyl groups, substituted cycloalkyl groups, aryl groups, and substituted aryl groups. In certain embodiments, $R_4$ is $S(=O)_2R_e$, wherein $R_e$ is chosen from alkyl groups, perhaloalkyl groups, aryl groups, and substituted aryl groups. In certain embodiments, $R_4$ is chosen from methanesulfonate, trifluoromethanesulfonate, and p-toluenesulfonate.

In certain embodiments, the method comprises reacting a compound chosen from compounds having formula (ii-c):

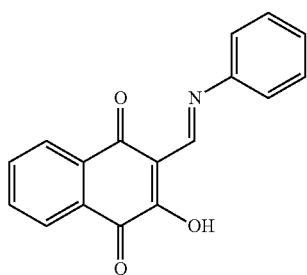

ii-c salts and solvates thereof.

In certain embodiments, $R_3$ is a substituted alkyl group. In certain embodiments, $R_3$ is

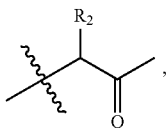

, wherein $R_2$ is a leaving group. In certain embodiments, the method comprises reacting a compound chosen from compounds having formula (ii-d):

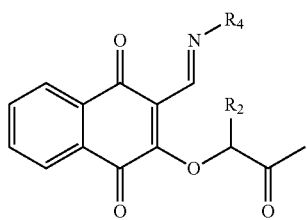

ii-d salts and solvates thereof, wherein $R_2$ is a leaving group, and $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, $C(=O)R_g$, $S(=O)_2R_e$, $P(=O)_2R_e$, $C(=O)OR_e$, $C(=O)NR_bR_c$, $S(=O)_2NR_bR_c$, and $P(=O)_2NR_bR_c$;

wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, $R_2$ is chosen from H, halides, sulfonates (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), an azide, carboxylates (e.g., —COOH or —COO⁻), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, $R_2$ is chosen from H, halides, carboxylates (e.g., —COOH or —COO⁻), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, $R_2$ is chosen from H, Cl, Br, I, —COOH, —COO⁻, methoxycarboxylate, ethoxycarboxylate, isopropoxycarboxylate, tert-butoxycarboxylate, phenoxycarboxylate, and methylphenoxycarboxylate. In certain embodiments, $R_2$ is chosen from H, Cl, Br, —COOH, —COO⁻, methoxycarboxylate, ethoxycarboxylate, isopropoxycarboxylate, and tert-butoxycarboxylate. In certain embodiments, $R_2$ is H. In certain embodiments, $R_2$ is tert-butoxycarboxylate.

In certain embodiments, $R_4$ is chosen from alkyl groups, substituted alkyl groups, cycloalkyl groups, substituted cycloalkyl groups, heterocycle groups, substituted heterocycle groups, aryl groups, and substituted aryl groups. In certain embodiments, $R_4$ is chosen from alkyl groups, cycloalkyl groups, heterocycle groups, and aryl groups. In certain embodiments, $R_4$ is chosen from methyl, ethyl, isopropyl, tert-butyl, cyclopentyl, cyclohexyl, cycloheptyl, phenyl, pyridyl, and pyrrolyl. In certain embodiments, $R_4$ is chosen from phenyl, pyridyl, and pyrrolyl. In certain embodiments, $R_4$ is phenyl.

In certain embodiments, the method comprises reacting a compound chosen from compounds having formula (ii-e):

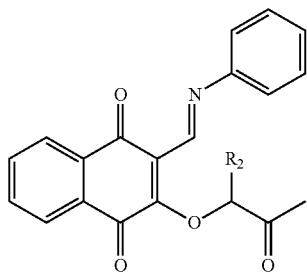

ii-e salts and solvates thereof, wherein $R_2$ is a leaving group.

In certain embodiments, $R_2$ is chosen from H, halides, sulfonates (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), an azide, carboxylates (e.g., —COOH or —COO$^-$), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, $R_2$ is chosen from H, halides, carboxylates (e.g., —COOH or —COO$^-$), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, $R_2$ is chosen from H, Cl, Br, I, —COOH, —COO$^-$, methoxycarboxylate, ethoxycarboxylate, isopropoxycarboxylate, tert-butoxycarboxylate, phenoxycarboxylate, and methylphenoxycarboxylate. In certain embodiments, $R_2$ is chosen from H, Cl, Br, —COOH, —COO$^-$, methoxycarboxylate, ethoxycarboxylate, isopropoxycarboxylate, and tert-butoxycarboxylate. In certain embodiments, $R_2$ is H. In certain embodiments, $R_2$ is tert-butoxycarboxylate.

In certain embodiments, X is O. In certain embodiments, the method comprises reacting a compound having formula (ii-f):

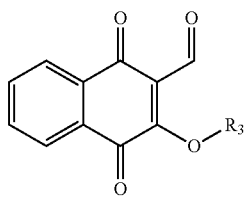

ii-f salts and solvates thereof,
wherein $R_3$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, $R_3$ is hydrogen. In certain embodiments, the method comprises reacting a compound having formula (ii-g):

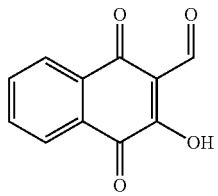

ii-g salts and solvates thereof.

In certain embodiments, $R_3$ is chosen substituted alkyl groups. In certain embodiments, $R_3$ is

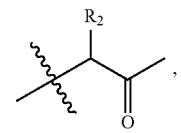

wherein $R_2$ is a leaving group. In certain embodiments, the method comprises reacting a compound chosen from compounds having formula (ii-h):

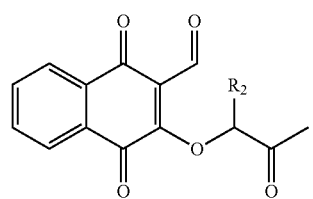

ii-h salts and solvates thereof, wherein $R_2$ is a leaving group.

In certain embodiments, $R_2$ is chosen from H, halides, sulfonates (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), an azide, carboxylates (e.g., —COOH or —COO$^-$), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, $R_2$ is chosen from H, halides, carboxylates (e.g., —COOH or —COO$^-$), alkoxycarboxylates (e.g., methoxycarboxylate, ethoxycarboxylate, isopropoxycarboxylate, or tert-butoxycarboxylate), or aroxycarboxylates (e.g., phenoxycarboxylate, methylphenoxycarboxylate). In certain embodiments, $R_2$ is chosen from H, Cl, Br, I, —COOH, —COO$^-$, methoxycarboxylate, ethoxycarboxylate, isopropoxycarboxylate, tert-butoxycarboxylate, phenoxycarboxylate, and methylphenoxycarboxylate. In certain embodiments, $R_2$ is chosen from H, Cl, Br, —COOH, —COO$^-$, methoxycarboxylate, ethoxycarboxylate, isopropoxycarboxylate, and tert-butoxycarboxylate. In certain embodiments, $R_2$ is H. In certain embodiments, $R_2$ is tert-butoxycarboxylate.

In certain embodiments, the method comprises reacting a compound chosen from compounds having formula (ii-i):

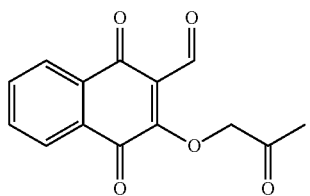

ii-i salts and solvates thereof.

In certain embodiments, the method comprises reacting the compound (ii) with a nucleophile. For example, the nucleophile can be a Michael donor. In certain embodiments, the method comprises reacting a compound having formula (ii) with a compound having formula (iii):

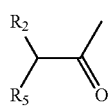

iii wherein $R_2$ and $R_5$ each independently is a leaving group.

In certain embodiments, $R_2$ is chosen from H, halides, sulfonates (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), an azide, carboxylates (e.g., —COOH or —COO$^-$), alkoxycarboxylates (e.g., methoxycarboxylate, ethoxycarboxylate, isopropoxycarboxylate, or tert-butoxycarboxylate), and aryloxycarboxylates (e.g., phenoxycarboxylate, methylphenoxycarboxylate). In certain embodiments, $R_2$ is chosen from H, halides, carboxylates (e.g., —COOH or —COO$^-$), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, $R_2$ is chosen from H, Cl, Br, I, —COOH, —COO$^-$, methoxycarboxylate, ethoxycarboxylate, isopropoxycarboxylate, tert-butoxycarboxylate, phenoxycarboxylate, and methylphenoxycarboxylate. In certain embodiments, $R_2$ is chosen from H, Cl, Br, —COOH, and —COO$^-$. In certain embodiments, $R_2$ is H.

In certain embodiments, $R_2$ is —C(O)OR$_a$, where R$_a$ is chosen from hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, alkynyl groups, substituted alkynyl groups, heterocycle groups, substituted heterocycle groups, aryl groups, and substituted aryl groups. In certain embodiments, $R_2$ is —C(O)OR$_a$, where R$_a$ is chosen from hydrogen, alkyl groups, and substituted alkyl groups. In certain embodiments, $R_2$ is —C(O)OR$_a$, where R$_a$ is chosen from hydrogen, methyl, ethyl, propyl, isopropyl, butyl, and tert-butyl. In certain embodiments, $R_2$ is —C(O)OH, —C(O)OCH$_3$, —C(O)OCH$_2$CH$_3$, —C(O)OCH(CH$_3$)$_2$, or —C(O)OC(CH$_3$)$_3$.

In certain embodiments, $R_5$ is chosen from halides, sulfonates, an azide, quaternary ammonium groups, and OR$_a$, where R$_a$ is chosen from hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, alkynyl groups, substituted alkynyl groups, heterocycle groups, substituted heterocycle groups, aryl groups, and substituted aryl groups. In certain embodiments, $R_5$ is chosen from Cl, Br, and I. In certain embodiments, $R_5$ is Cl. In certain embodiments, $R_5$ is Br. In certain embodiments, $R_5$ is chosen from optionally substituted $C_1$-$C_6$ alkanesulfonates and optionally substituted $C_7$-$C_{12}$ alkylbenzenesulfonates. In certain embodiments, $R_4$ is —N=N. In certain embodiments, $R_4$ is Br. In certain embodiments, $R_5$ is chosen from methanesulfonate, trifluoromethanesulfonate, and p-toluenesulfonate. In certain embodiments, $R_5$ is chosen from quaternary ammonium groups. In certain embodiments, $R_5$ is pyridinium or substituted pyridinium group.

In certain embodiments, the method comprises reacting a compound chosen from compounds having formula (ii) with a compound having formula (iii-a):

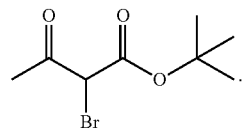

iii-a

In certain embodiments, the method comprises reacting a compound having formula (ii) with a compound having formula (iii-b):

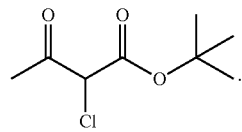

iii-b

In certain embodiments, the method comprises reacting a compound having formula (ii) with a compound having formula (iii-c):

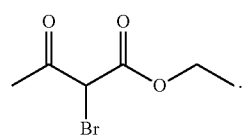

iii-c

In certain embodiments, the method comprises reacting a compound having formula (ii) with a compound having formula (iii-d):

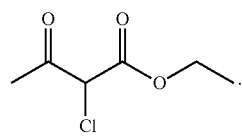

iii-d

In certain embodiments, the method comprises reacting a compound having formula (ii) with a compound chosen from compounds having formula (iii-e):

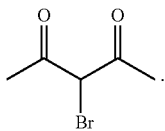

iii-e

In certain embodiments, the method comprises reacting a compound having formula (ii) with a compound having formula (iii-f):

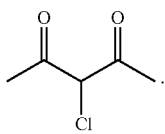

iii-f

In certain embodiments, the method comprises reacting a compound having formula (ii) with a compound having formula (iii-g):

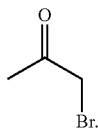

iii-g

In certain embodiments, the method comprises reacting a compound having formula (ii) with a compound having formula (iii-h):

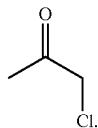

iii-h

In certain embodiments, the method comprises reacting a compound having formula (ii) with a compound having formula (iii-i):

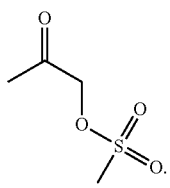

iii-i

In certain embodiments, the method comprises reacting a compound having formula (ii) with a compound having formula (iii-j):

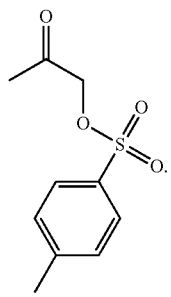

iii-j

In certain embodiments, the method comprises reacting a compound having formula (ii) with a compound having formula (iii-k):

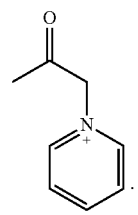

iii-k

In certain embodiments, the ratio of the compound having formula (iii) to the compound having formula (ii) is from about 0.1 to about 10. For example, the ratio is from about 0.5 to about 5, from about 0.8 to about 2.5, about 1, about 1.2, about 1.5, about 1.8, about 2, about 2.2, or about 2.5. In certain embodiments, the ratio is about 1.5.

In certain embodiments, the reaction comprises converting a compound of formula (ii) to a compound of formula (i) in the presence of a base. For example, the base can be an inorganic base or an organic base. In certain embodiments, the base comprises a base chosen from LiOH, NaOH, KOH, $Na_2CO_3$, $NaHCO_3$, $K_2CO_3$, $KHCO_3$, $Na_3PO_4$, $Na_2HPO_4$, $NaH_2PO_4$, $K_3PO_4$, $K_2HPO_4$, $KH_2PO_4$, $LiOCH_3$, $NaOCH_3$, $KOCH_3$, $LiOCH_2CH_3$, $NaOCH_2CH_3$, $KOCH_2CH_3$, $LiOC(CH_3)_3$, $NaOC(CH_3)_3$, $KOC(CH_3)_3$, ammonia, triethylamine (TEA), diisopropylethylamine (DIPEA), triethanolamine, imidazole, benzimidazole, pyridine, histidine, tetramethylammonium hydroxide, or tetrabutylammonium hydroxide. In certain embodiments, the base comprises a base chosen from $NaHCO_3$, $KHCO_3$, $Na_3PO_4$, $Na_2HPO_4$, $K_3PO_4$, $K_2HPO_4$, $LiOCH_2CH_3$, $NaOCH_2CH_3$, $KOCH_2CH_3$, $LiOC(CH_3)_3$, $NaOC(CH_3)_3$, $KOC(CH_3)_3$, triethylamine (TEA), diisopropylethylamine (DIPEA), and triethanolamine. In certain embodiments, the base comprises $NaHCO_3$. In certain embodiments, the base comprises $KHCO_3$. In certain embodiments, the base comprises $Na_2HPO_4$. In certain embodiments, the base comprises $K_2HPO_4$. In certain embodiments, the base comprises $LiOC(CH_3)_3$. In certain embodiments, the base comprises $NaOC(CH_3)_3$. In certain embodiments, the base comprises $KOC(CH_3)_3$. In certain embodiments, the base comprises triethylamine (TEA). In certain embodiments, the base comprises diisopropylethylamine (DIPEA). In certain embodiments, the base comprises triethanolamine.

In certain embodiments, the method comprises converting a compound chosen from compounds of formula (ii) to the dihydronaphthofuran derivative chosen from compounds of formula (i) in a solvent. In certain embodiments, the solvent is chosen from protic solvents or aprotic solvents. In certain embodiments, the solvent is chosen from water-miscible solvents. In certain embodiments, the solution comprises a solvent chosen from organic acids, alcohols, esters, amines, amides, aminoalcohols, ethers, sulfoxides, and heteroaromatics. In certain embodiments, the solution comprises a solvent chosen from acetone, acetonitrile, dimethylformamide (DMF), dimethylacetamide (DMA), N-methylpyrrolidone (NMP), dimethylimidazolidinone (DMI), dimethylsulfoxide (DMSO), dioxane, methanol, ethanol, propanol, iso-propanol, pyridine, and tetrahydrofuran. In certain embodiments, the solution comprises a solvent chosen from dimethylformamide (DMF), dimethylacetamide (DMA), N-methylpyrrolidone (NMP), and dimethylsulfoxide (DMSO). In certain embodiments, the solution comprises acetonitrile. In certain embodiments, the solution comprises dimethylacetamide (DMA). In certain embodiments, the solution comprises dimethylformamide (DMF). In certain embodiments, the solution comprises N-methylpyrrolidone (NMP). In certain embodiments, the solution comprises dimethylsulfoxide (DMSO). In certain embodiments, the solution comprises dimethylimidazolidinone (DMI).

In certain embodiments, the solution comprises a water-immiscible solvent. For example, in certain embodiments, the solution comprises a solvent chosen from toluene, ether, tetrahydrofuran (THF), methyl-tert-butylether, methyl-tetrahydrofuran, ethyl formate, ethyl acetate, propyl acetate, isopropyl acetate, and t-butyl acetate.

In certain embodiments, the method comprises providing the compound chosen from compounds having formula (ii-c) and a base (e.g., diisopropylethylamine (DIPEA) in a solvent (e.g., dimethylformamide (DMF)). In certain embodiments, the method comprises heating the mixture. In certain embodiments, the mixture is heated to from about 30° C. to about 70° C. In certain embodiments, the mixture is heated to about 30° C., about 35° C., about 40° C., about 45° C., about 50° C., about 55° C., about 60° C., about 65° C., or about 70° C. In certain embodiments, the method comprises providing the nucleophile (iii-a).

In certain embodiments, the method comprises converting a compound having formula (iv):

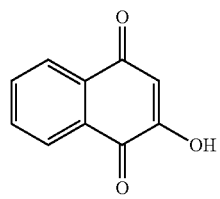

iv salts and solvates thereof, to a compound chosen from compounds having formula (ii).

In certain embodiments, the method comprises reacting a 2-hydroxynaphthalene-1,4-dione compound having formula (iv) with a compound of formula (v):

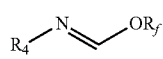

v where $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, $C(=O)R_e$, $S(=O)_2R_e$, $P(=O)_2R_e$, $C(=O)OR_e$, $C(=O)NR_bR_c$, $S(=O)_2NR_bR_c$, and $P(=O)_2NR_bR_c$;

wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_f$ and $R_g$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

In certain embodiments, $R_f$ is chosen from alkyl groups, substituted alkyl groups, cycloalkyl groups, substituted cycloalkyl groups, alkenyl groups, substituted alkenyl groups, cycloalkenyl groups, substituted cycloalkenyl groups, alkynyl groups, substituted alkynyl groups, heterocycle groups, substituted heterocycle groups, aryl groups, and substituted aryl groups. In certain embodiments, $R_f$ is chosen from alkyl groups and substituted alkyl groups. In certain embodiments, $R_f$ is chosen from cycloalkyl groups and substituted cycloalkyl groups. In certain embodiments, $R_f$ is chosen from aryl groups and substituted aryl groups. In certain embodiments, $R_f$ is chosen from methyl, ethyl, isopropyl, tert-butyl, cyclohexyl, and phenyl. In certain embodiments $R_f$ is ethyl.

In certain embodiments, $R_4$ is chosen from alkyl groups, substituted alkyl groups, cycloalkyl groups, substituted cycloalkyl groups, heterocycle groups, substituted heterocycle groups, aryl groups, and substituted aryl groups. In certain embodiments, $R_4$ is chosen from alkyl groups, cycloalkyl groups, heterocycle groups, and aryl groups. In certain embodiments, $R_4$ is chosen from methyl, ethyl, isopropyl, tert-butyl, cyclopentyl, cyclohexyl, cycloheptyl, phenyl, pyridyl, and pyrrolyl. In certain embodiments, $R_4$ is chosen from phenyl, pyridyl, and pyrrolyl. In certain embodiments, $R_4$ is phenyl.

In certain embodiments, the compound of formula (v) is a compound of formula (v-a):

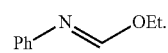

v-a

In certain embodiments, the method comprises converting a 2-hydroxynaphthalene-1,4-dione chosen from compounds of formula (iv) to a compound of formula (ii) in a solvent. For example, the solvent can be chosen from toluene, 1,2-dicholorbenzene, xylene, anisole, acetone, acetonitrile, ethyl acetate, isopropyl acetate, dimethylformamide (DMF), N-methylpyrrolidone (NMP), dimethylimidazolidinone (DMI), dimethylsulfoxide (DMSO), dioxane, methanol, ethanol, propanol, iso-propanol, formic acid, acetic acid, propanoic acid, pyridine, and tetrahydrofuran. In certain embodiments, the solvent is chosen from 1,2-dicholorbenzene, xylene, anisole, dimethylformamide (DMF), N-methylpyrrolidone (NMP), dimethylimidazolidinone (DMI), and dimethylsulfoxide (DMSO).

In certain embodiments, the method comprises converting a compound of formula (iv) to a compound of formula (ii) at a temperature. For example, in certain embodiments, the temperature can be from about 40° C. to about 170° C., from about 50° C. to about 150° C., from about 60° C. to about 130° C., or from about 70° C. to about 110° C. In certain embodiments, the method comprises converting a compound of formula (iv) to a compound of formula (ii) at about 70 to about 75° C., about 75 to about 80° C., about 80 to about 85° C., about 85 to about 90° C., about 90 to about 95° C., about 95 to about 100° C., about 100 to about 105° C., or about 105 to about 110° C.

Another aspect of the present disclosure relates to methods of preparing a compound of formula (I):

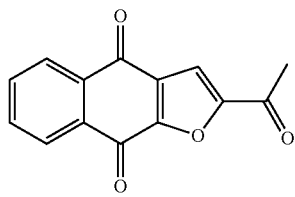

I prodrugs, derivatives, pharmaceutically acceptable salts of any of the foregoing, and solvates of any of the foregoing.

In certain embodiments, one of the methods comprises providing a solution of a compound of formula (I). In certain embodiments, the solution of the compound of formula (I) comprises anisole. In certain embodiments, the ratio (e.g., the volume-to-mass ratio) of anisole to the compound of formula (I) is from about 1 to about 30, about 2 to about 25, about 5 to about 25, about 10 to about 20, about 5, about 8, about 10, about 12, about 13, about 14, about 15, about 16, about 17, about 18, about 19, or about 20.

In certain embodiments, the method comprises providing the solution of the compound formula (I) at a first temperature. In certain embodiments, the first temperature is not lower than about 70° C., about 80° C., about 90° C., about 100° C., about 105° C., about 110° C., about 115° C., about 120° C., about 130° C., about 140° C., or not lower than about 150° C. In certain embodiments, the first temperature is about 100° C., about 105° C., about 110° C., about 115° C., about 120° C., or about 100° C. to about 115° C.

In certain embodiments, the method comprises providing the solution of the compound of formula (I) at a second temperature. In certain embodiments, the second temperature is not higher than about 80° C., about 70° C., about 60° C., about 50° C., about 40° C., about 30° C., about 20° C., about 10° C., about 5° C., or not higher than about 0° C.

In certain embodiments, the second temperature is about 0° C. In certain embodiments, the second temperature is about 1° C. In certain embodiments, the second temperature is about 2° C., about 3° C., about 4° C., about 5° C., about 6° C., about 7° C., about 8° C., about 9° C., about 10° C., about 11° C., about 12° C., about 13° C., about 14° C., or about 15° C. In certain embodiments, the second temperature is from about 0° C. to about 5° C.

In certain embodiments, the method comprises providing the solution of the compound of formula (I) in the presence of a first agent. In certain embodiments, the first agent comprises silica gel. In certain embodiments, the ratio (e.g., the mass-to-mass ratio) of the first agent to the compound of formula (I) is from about 0.1 to about 10, about 0.2 to about 8, about 0.5 to about 5, about 0.5 to about 3, about 0.5 to about 2, about 0.5, about 0.8. In certain embodiments, the ratio of the first agent to the compound chosen from compounds of formula (I) is about 1.0, about 1.1, about 1.2, about 1.3, about 1.4, about 1.5, about 1.6, about 1.7, about 1.8, about 1.9, or about 2.0.

Another aspect of the present disclosure relates to certain compounds that can be used to prepare compounds having formula (I). In certain embodiments, provided herein is a compound chosen from compounds having formula (i)

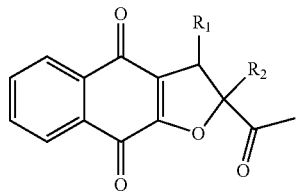

i salts and solvates thereof, wherein $R_1$ and $R_2$ each independently is a leaving group.

In certain embodiments, $R_1$ is selected from the group consisting of halides, $OR_a$, and $NR_bR_c$; where $R_a$ is selected from the group consisting of hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, alkynyl groups, substituted alkynyl groups, heterocycle groups, substituted heterocycle groups, aryl groups, and substituted aryl groups; and $R_b$ and $R_c$ each is independently selected from the group consisting of hydrogen, alkyl groups, substituted alkyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group. In certain embodiments, $R_1$ is selected from the group consisting of Cl, Br, I, $OR_a$, and $NR_bR_c$; where $R_a$ is selected from the group consisting of hydrogen, alkyl groups, substituted alkyl groups, cycloalkyl groups, substituted cycloalkyl groups, heterocycle groups, substituted heterocycle groups, aryl groups, and substituted aryl groups; and $R_b$ and $R_c$ each is independently chosen from hydrogen, alkyl groups, substituted alkyl groups, cycloalkyl groups, substituted cycloalkyl groups, heterocycle groups, substituted heterocycle groups, aryl groups, and substituted aryl groups. In certain embodiments, $R_1$ is selected from the group consisting of Cl, Br, I, and $NR_bH$; where $R_b$ is selected from the group consisting of alkyl groups, substituted alkyl groups, cycloalkyl groups, substituted cycloalkyl groups, aryl groups, and substituted aryl groups. In certain embodiments, $R_1$ is $NR_bH$, where $R_b$ is phenyl or substituted phenyl.

In certain embodiments, $R_2$ is selected from the group consisting of halides, sulfonates (e.g., an optionally substituted $C_1$-$C_6$ alkanesulfonate, such as methanesulfonate and trifluoromethanesulfonate, or an optionally substituted $C_7$-$C_{12}$ alkylbenzenesulfonate, such as p-toluenesulfonate), an azide, carboxylates (e.g., —COOH or —COO⁻), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, $R_2$ is selected from the group consisting of halides, carboxylates (e.g., —COOH or —COO⁻), alkoxycarboxylates (e.g., methoxycarboxylate, ethoxycarboxylate, isopropoxycarboxylate, or tert-butoxycarboxylate), and aroxycarboxylates (e.g., phenoxycarboxylate, methylphenoxycarboxylate). In certain embodiments, $R_2$ is selected from the group consisting of Cl, Br, I, —COOH, —COO⁻, methoxycarboxylate, ethoxycarboxylate, isopropoxycarboxylate, tert-butoxycarboxylate, phenoxycarboxylate, and methylphenoxycarboxylate. In certain embodiments, $R_2$ is selected from the group consisting of Cl, Br, —COOH, —COO⁻, methoxycarboxylate, ethoxycarboxylate, isopropoxycarboxylate, and tert-butoxycarboxylate. In certain embodiments, $R_2$ is tert-butoxycarboxylate.

In certain embodiments, the compound of formula (i) conforms to formula (i-a)

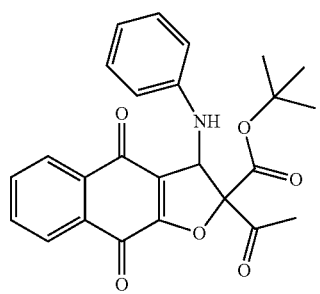

i-a salts and solvates thereof.

In certain embodiments, provided herein is a compound having formula (ii):

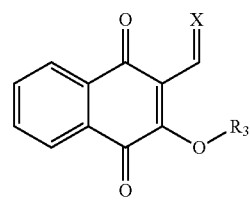

ii salts and solvates thereof;
wherein $R_3$ and X each is as defined herein.

In certain embodiments, provided herein is a compound chosen having formula (ii-a):

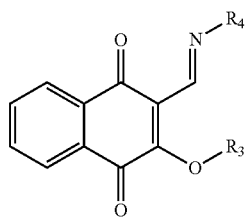

ii-a salts and solvates thereof,
wherein $R_3$ and $R_4$ each is as defined herein.

In certain embodiments, $R_3$ is hydrogen. In certain embodiments, provided herein is a compound having formula (ii-b):

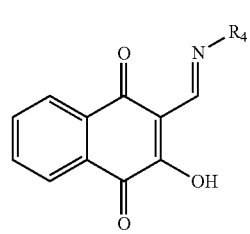

ii-b salts and solvates thereof, wherein $R_4$ is as defined herein.

In certain embodiments, provided herein is a compound having formula (ii-c):

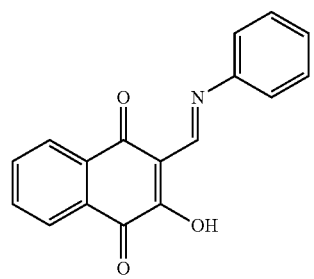

ii-c salts and solvates thereof.

In certain embodiments, provided herein is a compound having formula (ii-d):

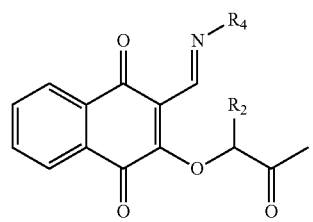

ii-d salts and solvates thereof,
wherein $R_2$ and $R_4$ each is as defined herein.

In certain embodiments, provided herein is a compound having formula (ii-e):

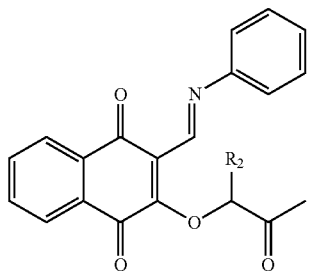

ii-e salts and solvates thereof, wherein $R_2$ is as defined herein.

In certain embodiments, provided herein is a compound having formula (ii-f):

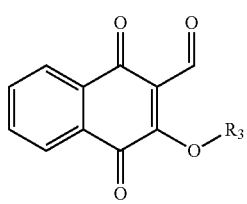

ii-f salts and solvates thereof, wherein $R_3$ is as defined herein.

In certain embodiments, provided herein is a compound having formula (ii-g):

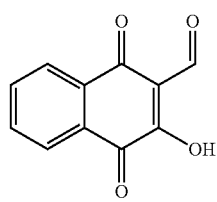

ii-g salts and solvates thereof.

In certain embodiments, provided herein is a compound having formula (ii-h):

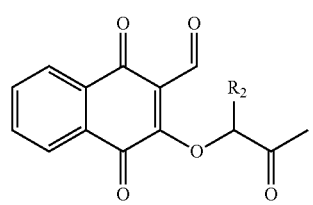

ii-h salts and solvates thereof, wherein $R_2$ is as defined herein.

In certain embodiments, provided herein is a compound having formula (ii-i):

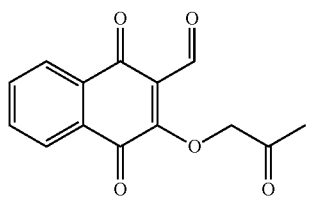

ii-i salts and solvates thereof.

In certain embodiments, provided herein is a compound having formula (iii):

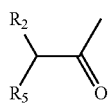

iii wherein $R_2$ and $R_4$ each is as defined herein.

In certain embodiments, provided herein is a compound chosen from compounds having formulae (iii-a) to (iii-k):

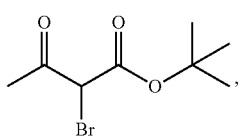

iii-a

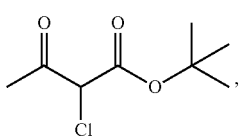

iii-b

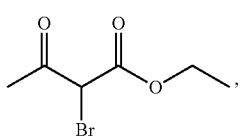

iii-c

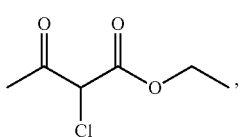

iii-d

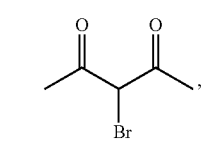

iii-e

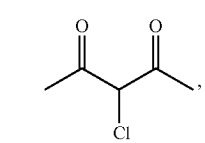

iii-f

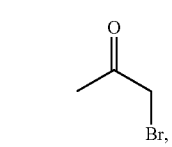

iii-g

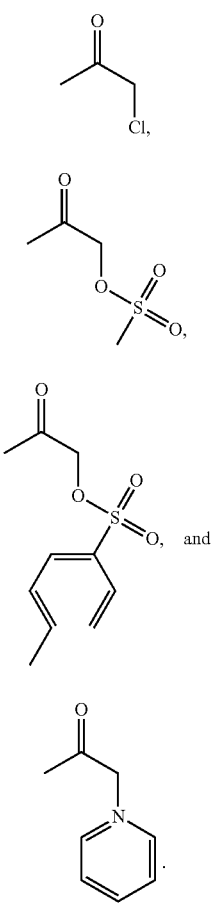

In certain embodiments, provided herein is a compound having formula (iv):

iv salts and solvates thereof.

In certain embodiments, provided herein is a compound having formula (v):

v wherein $R_4$ and $R_f$ each is as defined herein.

In certain embodiments, the compound having formula (v) conforms to formula v-a.

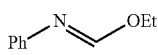

v-a

In certain embodiments, the present disclosure provides methods of preparing a compound of the present disclosure. In certain embodiments, the compound is prepared according to methods disclosed in PCT Patent Application Publication Numbers WO2009036099, WO2009036101, WO2011116398, and WO2011116399, which are each incorporated herein by reference in their entirety. In certain embodiments, a compound of the present disclosure is prepared by using the methods disclosed herein, together with synthetic methods known to one skilled in the art of organic synthesis, or variations thereof. In certain embodiments, a compound of the present disclosure is prepared by using methods known to one skilled in the art. It is understood that methods disclosed in WO2009036099, WO2009036101, WO2011116398, and WO2011116399, or herein, as well as those known to the skilled artisan, are for illustration purpose and, accordingly, do not in any way limit the scope of the appended claims.

Without being limited by any particular preparative methods, the present disclosure provides a method of preparing a compound of formula (I) of the present disclosure. In certain embodiments, the compound of formula (I) is prepared by a method shown in Scheme below, where $R_1$ and $R_2$ are as defined herein.

Scheme 1

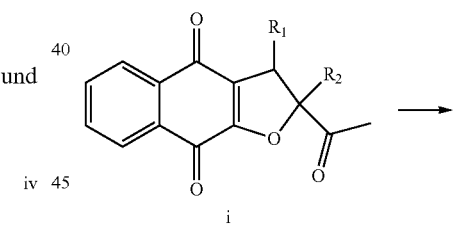

As shown in Scheme 1, in certain embodiments, the method comprises reacting a compound having formula (i).

In certain embodiments, the compound of formula (I) is prepared by a method shown in Scheme 2 below.

Scheme 2

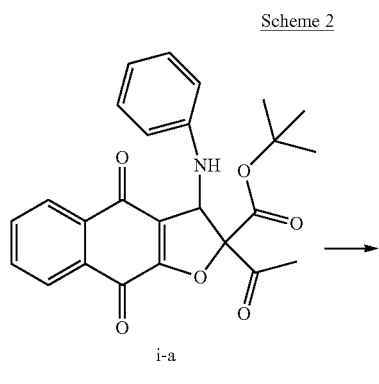

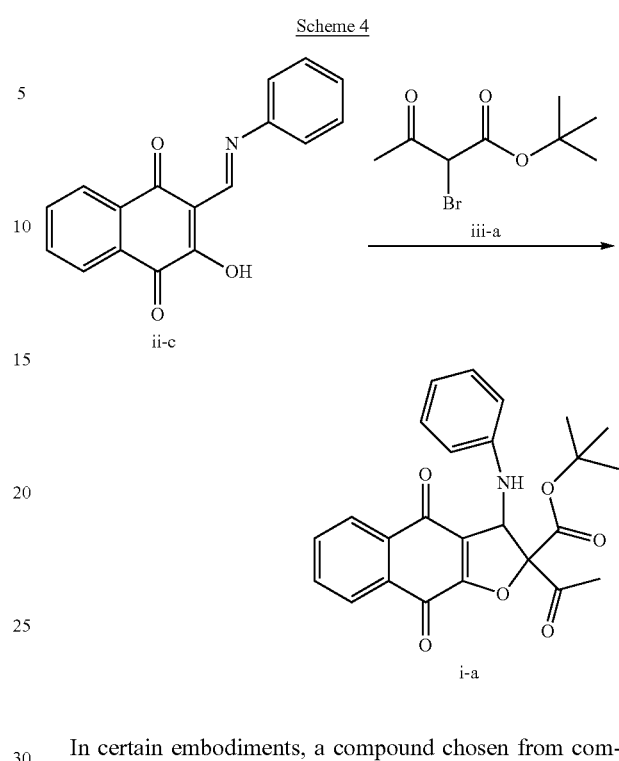

In certain embodiments, a compound chosen from compounds having formula (i) is prepared by a method shown in Scheme 3 below.

Scheme 3

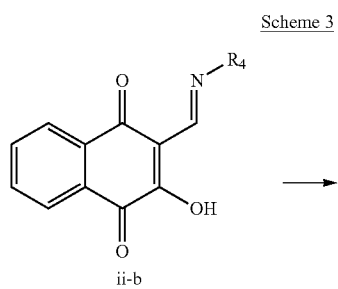

In certain embodiments, a compound having formula (i-a) is prepared by a method shown in Scheme 4 below.

In certain embodiments, a compound chosen from compounds having formula (ii) is prepared by a method shown in Scheme 5.

Scheme 5

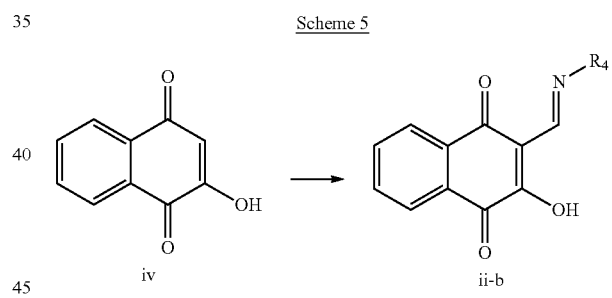

In certain embodiments, the method comprises reacting a compound having formula (iv) with a compound formula (v):

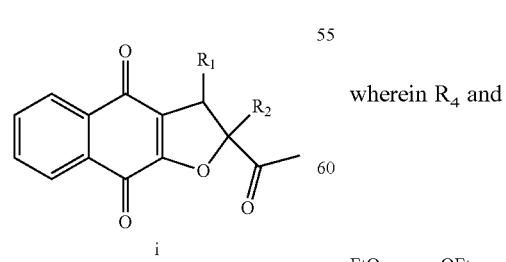

wherein $R_4$ and $R_f$ each is as defined herein.

EXAMPLES

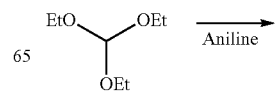

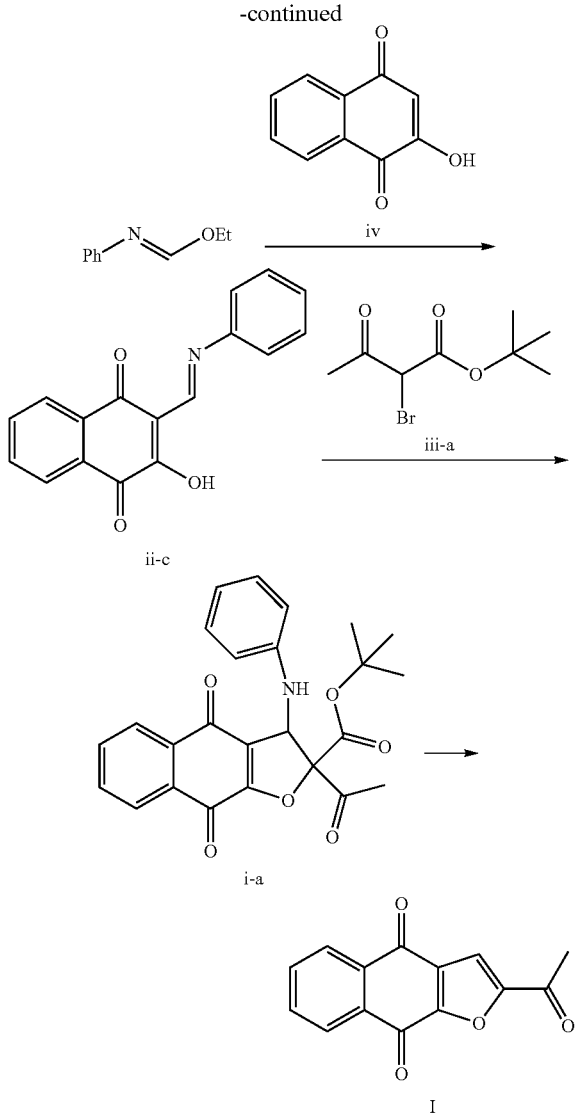

Example 1

Aniline (300 g, 3.22 mol) was added to a 1 L reactor containing triethyl orthoformate (790 mL, 1.5 eq) and HCl (0.01 eq, 10.68 mL 11% solution in methanol) at 23-31° C. over 0.5 h. The reaction mixture was heated from 30° C. to 120° C. with stripping off ethanol over 3 hours. Ethanol stripping was stopped and the mixture was cooled to 35° C. Precipitation occurred. The mixture was heated back to 120° C. The pressure was slowly reduced and ethanol/triethyl orthoformate mixture was collected from 700 mbar. The product was collected from 36 mbar and approximately 100 ml residue remained in the reactor after distillation. The residue solidified at 50° C. The solid was dissolved in methanol. The main crop (295.9 g, NMR assay 102%) and additional crop (63 g, NMR assay 97%) of ethyl N-phenyl-formimidate (v-a) were obtained.

Example 2

Compound (iv) (2-hydroxy-1,4-naphthoquinone, "HNQ") (83 g, 477 mmol) was heated in 620 mL of anisole to 110° C. Ethyl N-phenylformimidate (v-a, 100 g, 1.4 equivalents) was added in one portion. The flask was rinsed with 30 mL of anisole and the rinse was added to reaction mixture. Internal temperature dropped to 106° C. Slight boiling and almost instantaneous formation of an orange precipitate was observed after mixture was heated back to 110° C. An exotherm was observed and the mixture was heated to 121° C. The reaction mixture was maintained at 120° C. for 10 minutes and UPLC sample showed full conversion of HNQ at this point. The mixture was cooled to 22° C., and the resulting solid was filtered, rinsed with 250 mL of anisole and dried at 50° C./15 mbar for 16 h. A bright yellow, shiny, flaky solid (ii-c, 99.6 g, 75% yield, with UPLC purity 100%) was obtained.

B. Synthesis of Schiff base in anisole. HNQ at 90° C.—(10.0 g, 56.3 mmol) was heated in 70 mL of anisole to 90° C. under nitrogen atmosphere. Ethyl N-phenylformimidate (v-a, 2.7 g, 0.3 equivalents) was added dropwise over 15 minutes. Ethyl N-phenylformimidate (6.1 g, 0.7 eq) addition was continued over an hour. Crystallization started when about 0.5 eq. of ethyl-N-phenylformimidate was added. Full conversion of HNQ was observed 1 hour after completion of addition. Mixture was left to cool to room temperature over 2 hours. Schiff base (ii-c, 14.33 g, 90% yield, yellow solid, 100% purity by UPLC) was obtained by filtering the mixture and the solids rinsed with 70 mL of anisole and dried at 50° C./15 mbar for 16 h.

C. Synthesis of Schiff base in anisole at 70° C. Ethyl N-phenylformimidate (v-a, 9.42 g, 1.1 equivalents, assay 98.8%) was added in one portion to HNQ (10.0 g, 56.3 mmol) and was heated in 70 mL of anisole to 70° C. under nitrogen atmosphere. Crystallization started at 50° C. after 15 minutes. Full conversion of HNQ was observed 3 hours after completion of addition. Mixture was left to cool to room temperature over 2 hours. Schiff base was filtered, rinsed with 40 mL of anisole. Dried for 16 h at 50° C. at 15 mbar of pressure. Compound ii-c (15.19 g, 95% yield, and 99.6% purity by UPLC) was obtained as a golden-yellow solid.

D. Synthesis of Schiff base in 1,2-dichlorobenzene. Compound (iv) (65 g, 373 mmol) was dissolved in 750 mL of 1,2-dichlorobenzene at 110° C. Ethyl N-phenyl formimidate (va) (85.4 g, 1.5 equivalents) was added over 10 minutes. A full conversion of compound (iv) was observed after 20 minutes at 110-140° C. and 40 minutes at 140° C. The mixture was cooled to 55° C. Methylcyclohexane (100 mL) was added and the mixture was cooled to room temperature. The resulting solid was filtered off, washed with 300 mL of methylcyclohexane three times, and dried in a vacuum dryer at 15 mbar and 45° C. for 16 h. The Schiff base (iia, 96.8 g) was obtained as a fluffy yellow solid with UPLC purity 100% and NMR assay 99.1%. The yield corrected according to the NMR assay was determined to be 93%.

Synthesis of Schiff base in DMF. HNQ (iv, 5 g, 28.7 mmol) was heated in 50 mL of DMF to 110° C. Ethyl N-phenylformimidate (v-a, 6.42 g, 1.5 eq) was added dropwise. No boiling was observed at this point. The mixture was heated to 118° C. and formation of a dark solid was observed. The mixture was stirred for 5 minutes and a sample was obtained for UPLC analysis, which showed full conversion of HNQ. After cooling to 18° C., the mixture was filtered and the solid was rinsed with 120 mL of DMF, 60 mL of iPrOH and then dried in a vacuum chamber at 50° C./15 mbar for 17 h. The Schiff base (ii-c, 6.38 g, UPLC purity 100% by area) was obtained as a fluffy yellow solid. Reaction yield calculated by weight was determined to be 80%.

Example 3

DMF (40 mL) was added to Schiff base (ii-c, 10 g, 36.1 mmol) and micronized NaHCO$_3$ (12.12 g, 4 eq.). The mixture was heated to 44° C. and crude BrAA (iii-a, 12.83 g, 1.4 eq.) was added in one portion. The mixture was maintained at 45-50° C. 0.2% of unreacted Schiff base (ii-c) was detected in reaction mixture after 3 h. The mixture was filtered and the collected solids were washed with 15 mL of DMF. The crude compound (i-a, 71.41 g, yield 83%) solution was obtained.

Example 4

The crude compound (i-a) crude solution (337.3 g) in DMF was concentrated to 166.3 g (Ti=50° C./19 mbar, reduced by 50%). A minor amount of white mineral salt precipitation was observed. The concentrated mixture (including precipitated mineral salt) was added to 340 mL of sulfuric acid/acetic acid (1:1) mixture over 1 h at 18-22° C. Gas emission was observed. Formation of a yellow precipitate was observed after ~¾ of the mixture was added. The resulting solid was filtered off, the slurry was washed on filter with 500 mL of water and then with 250 mL of iPrOH, and then solid was dried at 50° C./15 mbar for 18 h. A mustard-yellow powder (24.3 g, 99.6% by area, 97% isolated yield corrected to NMR assay) was obtained.

Example 5a

2-Hydroxynaphthalene-1,4-dione (iv, 5 g, 28.7 mmol) was dissolved in 50 mL of DMI at 80-90° C. The solution was heated to 140° C. Ethyl N-phenylformimidate (va, 6.62 g, 1.5 eq) was added slowly to the heated solution. A full conversion of 2-hydroxynaphthalene-1,4-dione (iv) and formation of fine precipitate was observed after 15 minutes.

The mixture was cooled to 45° C. A thick slurry was formed (black solution and yellow precipitate). This slurry was used in the next step without any purification.

Example 5b

DMI (20 mL), NaHCO$_3$ (14.11 g, 6 eq), and tert-butyl-2-bromo-acetoacetate (iii-a) (12.46 g, 1.5 eq) were added to the crude Schiff base (ii-c) mixture in DMI at 45° C. A full conversion of Schiff base (ii-c) was observed after 6 h at 45-50° C.

The inorganic salt was filtered off and rinsed with 20 mL of DMI. The yield over two steps corrected according to the NMR assay was 57%. The filtrate containing the dihydronaphthofuran derivative (i-a) was used in the next step without any further purification.

Example 5c

Acetic acid (100 mL) and sulfuric acid (100 mL) were mixed and cooled to 20° C. in a water bath. The filtrate from the previous step (Example 5b, 100 g, 6.86% solution in DMI) was added dropwise to the mixture over 1.5 h at 18-24° C. A black, clear, and thick solution was observed.

The resulting mixture was poured into ice/water mixture (300 mL) at 0-15° C. and slowly stirred for 45 minutes. A very fine precipitate was filtered off, rinsed with water, and dried in vacuum chamber at 50° C./15 mbar for 15 h. A brown precipitate (compound (I), 3.95 g) was obtained. Assay by NMR 68.1%. Step 3 yield corrected to NMR assay was 71%.

The isolated yield from 2-hydroxynaphthalene-1,4-dione (iv) corrected to NMR assay was 39%. With the isolated Schiff base (ii-c) and alkylation in DMF, the isolated yield of crude compound (I) over three steps was 71%.

Example 6

Compound (I) (200 g, 1×, crude-1) and silica gel (1.3×, 100-200 mesh) were charged into a reactor and then anisole (15 V) was added. The reaction mixture was heated to 100-110° C. and stirred for 1-2 h. The reaction mixture was then cooled to 80° C., and filtered through 0.5~1.0× of diatomite. The solids were combined with anisole (3 V) at 80-90° C. and then filtered. The combined filtrate was heated to 80-90° C. and then slowly cooled to 0-5° C. The solids were filtered and dried at 50-60° C. under vacuum to give compound (I) (crude-2). The crude-2 was triturated in hot EtOAc (25 V) to give compound (I) (75% yield form crude-1).

Compound (I) (3 g, crude, assay 91.5%) was combined with anisole (90 mL, 30 vol) at 100-110° C. Activated carbon (100 mesh, 40% w/w) was added and the mixture was stirred for 1 h. The carbon was filtered hot through a carton-board lined glass filter and washed with 20 mL of hot anisole. The resulting filtrate was concentrated to ~13 vol at 70° C./30 mbar. The resulting mixture was reheated to 110° C. and was then cooled to 0° C. over 2 h. After cooling, the mixture was filtered and the collected solids were rinsed with 20 mL of cold anisole and dried in vacuum chamber at 50° C./15 mbar for 18 h. 2.4 g of Fine, orange-yellow needles (compound (I), 2.4 g) were obtained. UPLC purity was determined to be 100% by area. The purity was determined by the NMR assay to be 99.1% and the yield was determined to be 87%.

Those skilled in the art will recognize, or be able to ascertain using no more than routine experimentation, many equivalents to the specific embodiments of the present disclosure described herein. Such equivalents are intended to be encompassed by the following claims.

What is claimed:

1. A method of making a compound having formula (I):

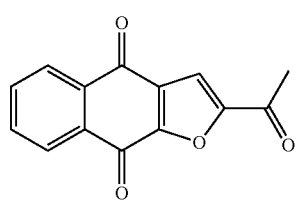

I or a prodrug, a pharmaceutically acceptable salt, or a solvate thereof;

comprising reacting a compound having formula (i):

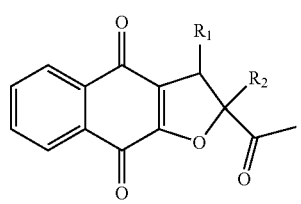

i or a salt or solvate thereof, with an acid;
wherein $R_1$ and $R_2$ each independently is a leaving group.

2. The method of claim 1, wherein
$R_1$ is chosen from halides, $OR_a$, and $NR_bR_c$; where $R_a$ is chosen from hydrogen, alkyl groups, substituted alkyl groups, cycloalkyl groups, substituted cycloalkyl groups, alkenyl groups, substituted alkenyl groups, cycloalkenyl groups, substituted cycloalkenyl groups, alkynyl groups, substituted alkynyl groups, heterocycle groups, substituted heterocycle groups, aryl groups, and substituted aryl groups; and $R_b$ and $R_c$ each is independently chosen from hydrogen, alkyl groups, substituted alkyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group.

3. The method of claim 1, wherein $R_1$ is $NR_bH$, where $R_b$ is phenyl or substituted phenyl.

4. The method of claim 1, wherein $R_2$ is chosen from halides, carboxylates, alkoxycarboxylates, and aryloxycarboxylates.

5. The method of claim 1, wherein $R_2$ is chosen from Cl, Br, —COOH, —COO—, methoxycarboxylate, ethoxycarboxylate, isopropoxycarboxylate, and tert-butoxycarboxylate.

6. The method of claim 1, wherein $R_2$ is tert-butoxycarboxylate.

7. The method of claim 1, wherein the compound having formula (i) has formula (i-a):

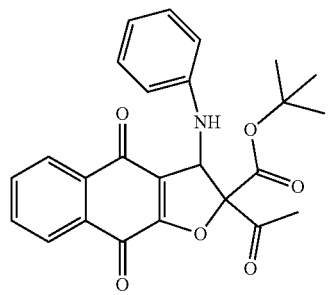

i-a or a salt or solvate thereof.

8. The method of claim 1, further comprising reacting a compound having formula (ii):

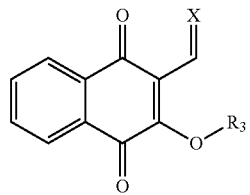

ii or a salt or solvate thereof;
wherein
X is O or N—$R_4$, and
$R_3$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups;

$R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, $C(=O)R_g$, $S(=O)_2R_e$, $P(=O)_2R_e$, $C(=O)OR_e$, $C(=O)NR_bR_c$, $S(=O)_2NR_bR_c$, and $P(=O)_2NR_bR_c$;

wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_g$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups;

with a compound having formula (iii):

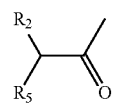

iii wherein $R_2$ and $R_5$ each independently is a leaving group.

9. The method of claim 8, wherein the compound having formula (ii) has the formula (ii-b)

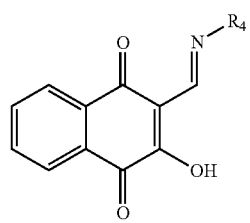

ii-b wherein $R_4$ is chosen from methyl, ethyl, isopropyl, tert-butyl, cyclopentyl, cyclohexyl, cycloheptyl, phenyl, pyridyl, and pyrrolyl.

10. The method of claim 8, wherein $R_4$ is phenyl.

11. The method of claim 8, wherein the compound having formula (ii) has formula (ii-c):

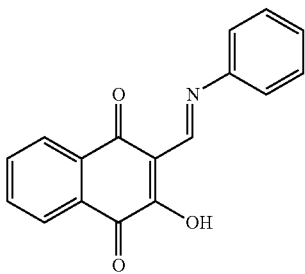

or a salt or solvate thereof.

12. The method of claim 11, wherein the compound having formula (iii) has the formula (iii-a):

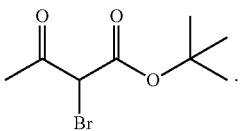

13. The method of claim 8, further comprising converting a 2-hydroxynaphthalene-1,4-dione having formula (iv):

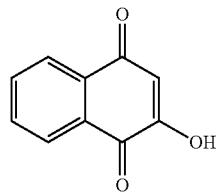

or a salt or solvate thereof, to the compound having formula (ii).

14. The method of claim 1, wherein the acid comprises an acid chosen from sulfuric acid ($H_2SO_4$), phosphoric acid ($H_3PO_4$), nitric acid ($HNO_3$), perchloric acid ($HClO_4$), hydrofluoric acid (HF), hydrochloric acid (HCl), hydrobromic acid (HBr), and hydroiodic acid (HI).

15. The method of claim 1, wherein the acid is sulfuric acid ($H_2SO_4$), phosphoric acid ($H_3PO_4$), or hydrochloric acid (HCl).

16. The method of claim 1, wherein the acid is chosen from formic acid, acetic acid, acetic anhydride, trifluoroacetic acid, trifluoroacetic anhydride, chloroacetic acid, and chloroacetic anhydride.

17. The method of claim 1, wherein the acid comprises an acid chosen from sulfuric acid ($H_2SO_4$), acetic acid, and acetic anhydride.

18. The method of claim 1, comprising reacting a solution of the compound having formula (i) with the acid.

19. The method of claim 18, wherein the solution comprises a solvent chosen from isopropyl acetate, dimethylformamide (DMF), N-methylpyrrolidone (NMP), and dimethylimidazolidinone (DMI).

20. The method of claim 8, comprising reacting the compound having formula (ii) in the presence of a base chosen from $NaHCO_3$, $KHCO_3$, $Na_3PO_4$, $Na_2HPO_4$, $K_3PO_4$, $K_2HPO_4$, $LiOCH_2CH_3$, $NaOCH_2CH_3$, $KOCH_2CH_3$, $LiOC(CH_3)_3$, $NaOC(CH_3)_3$, $KOC(CH_3)_3$, triethylamine (TEA), diisopropylethylamine (DIPEA), and triethanolamine.

21. The method of claim 13, comprising reacting the 2-hydroxynaphthalene-1,4-dione having formula (iv) with a compound of formula (v):

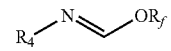

wherein $R_4$ is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, substituted aryl groups, $C(=O)R_g$, $S(=O)_2R_e$, $P(=O)_2R_e$, $C(=O)OR_e$, $C(=O)NR_bR_c$, $S(=O)_2NR_bR_c$, and $P(=O)_2NR_bR_c$;

wherein $R_b$ and $R_c$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups, or $R_b$ and $R_c$ together with the N to which they are bonded form a heterocycle group or a substituted heterocycle group;

$R_e$ is chosen from alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups; and $R_f$ and $R_g$ each independently is chosen from hydrogen, alkyl groups, substituted alkyl groups, alkenyl groups, substituted alkenyl groups, alkynyl groups, substituted alkynyl groups, cycloalkyl groups, substituted cycloalkyl groups, heterocycle groups, substituted heterocycle groups, aryl groups, and substituted aryl groups.

22. The method of claim 21, wherein $R_f$ is chosen from methyl, ethyl, propyl, isopropyl, butyl, and tert-butyl.

* * * * *